US007553956B2

(12) United States Patent
Fujii

(10) Patent No.: US 7,553,956 B2
(45) Date of Patent: Jun. 30, 2009

(54) POLYNUCLEOTIDE PROBE AND PRIMER FOR DETECTING BEER-CLOUDING LACTIC ACID BACTERIA AND METHOD OF DETECTING BEER-CLOUDING LACTIC ACID BACTERIA

(75) Inventor: Toshio Fujii, Yokohama (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 497 days.

(21) Appl. No.: 10/478,404

(22) PCT Filed: May 23, 2002

(86) PCT No.: PCT/JP02/05022

§ 371 (c)(1), (2), (4) Date: Nov. 21, 2003

(87) PCT Pub. No.: WO02/095028

PCT Pub. Date: Nov. 28, 2002

(65) Prior Publication Data
US 2004/0248115 A1    Dec. 9, 2004

(30) Foreign Application Priority Data
May 23, 2001    (JP)    ............... 2001-154085

(51) Int. Cl.
C07H 21/04    (2006.01)
C12Q 1/68    (2006.01)
(52) U.S. Cl. ...................... 536/24.32; 435/6
(58) Field of Classification Search ............ None
See application file for complete search history.

(56) References Cited

U.S. PATENT DOCUMENTS

| | | | | |
|---|---|---|---|---|
| 5,756,086 | A | * | 5/1998 | McClelland et al. ....... 424/93.2 |
| 2003/0165843 | A1 | * | 9/2003 | Shoshan et al. ................ 435/6 |

FOREIGN PATENT DOCUMENTS

| | | |
|---|---|---|
| EP | 890650 A2 | 1/1999 |
| WO | WO 01/23605 A | 4/2001 |

OTHER PUBLICATIONS

Whisstock, James et al. Prediction of protein function from protein sequence and structure. 2003. Quarterly Reviews of Biophysics. vol. 36 pp. 307-340.*
Fujii, T et al. Random amplified polymorphic DNA-PCR based cloning of markers to identify the beer spoilage strains of *L.Actobacillus brevis, Perdiococcus damnosus, Lactobacillus collinoides* and *Lactobacillus coryniformis*. 2005 Journal of Applied Microbiology. vol. 98 pp. 1209-1220.*
Database EMBL 'Online! Jun. 2, 1996, "Leuconostoc lactis plasmid pNZ63 lactose transport protein (lac5) gene, partial cds.", XP 002318131.

Elaine E. Vaughan et al., "The Lactose Transporter in Leuconostoc lactis Is a New Member of the LacS Subfamily of Galactoside-Pentose-Hexuronide Translocators", Applied and Environmental Microbiology, vol. 62, No. 5, May 1996, pp. 1574-1582.
Database EMBL 'Online! Jun. 9, 1993, "Mouse granuloma associated factor mRNA, complete cds.", XP002318132.
Database EMBL Online! Sep. 6, 1995, "Mus musculus clone pMG75 nonsatellite RNA sequence", XP002318133.
Databse EMBL Online! May 11, 2000, "Neurospora crassa DNA linkage group II BAC clone B208", XP002307888.
Database EMBL Online! Feb. 2, 1993, "A. caulinodans NtrY/NtrX DNA sequence" XP002307889.
Database EMBL 'Online!, Nov. 11, 1999, "H5_5052_B2_H12_T7A RPCI-11 Human Male BAC Library *Homo sapiens* genomic clone Plate= 8820 col. 24 Row=P, genomic survey sequence", XP002318134.
Database EMBL 'Onlinel, Sep. 19, 2000, "GSSBru1753 Brucella abortus random genomic library Brucella melitensis biovar Abortus genomic clone UU1753, DNA sequence", XP002318135.
Database EMBL 'Online! Dec. 10, 1999, "Chlamydomonas reinhardtii cDNA clone: CM011G12_r, 5'mRNA sequence", XP002318136.
Database EMBL 'Online! Jan. 19, 1998, "nw62d07 . s1 NCI_CGAP_GCB1 *Homo sapiens* cDNA clone Image: 1251181 3', mRNA sequence", XP002318137.
Database Geneseq 'Online! Sep. 10, 2001, "Human map-related biallelic marker SEQ ID No. 810. ", XP002318138.
Database EMBL 'Online! Aug. 3, 1999, "*Arabidopsis thaliana* DNA * Sequencing in Progress * BAC clone M28D5 (ESSAll project)", XP002318139.
Database EMBL 'Online! Nov. 9, 1999, "nbeb0016J13f CUGI Rice BAC Library (ECoRI) Oryza sativa genomic clone nbeb0016J13f, genomic survey sequence", XP002318140.
Database EMBL 'Online! Jul. 6, 1993, "Adenovirus type 12 DNA, complete genome", XP002318141.
Database EMBL 'Online! Feb. 20, 2000, "89780 MARC IBOV Bos Taurus cDNA 5', mRNA sequence," XP002318142.
Database EMBL 'Online! Aug. 24, 1993, "*A. thaliana* transcribed sequence; clone VCVDA03", XP002318143.
Database EMBL 'Online! Jan. 25, 2001, "3C6 cDNA library of 4-day-old Eucalyptus globulus bicostata-Pisolithus tinctorius cDNA 5' similar to hypothetical protein, mRNA sequence", XP002318144.
Database UniProt 'Online! Jul. 15, 1998, "Putative glycosyl transferase ykoT (EC 2.-.-.-)" XP002307345.
Database UniProt 'Online! Nov. 1, 1998, "Cytochrome Oxidase Subunit II", XP002318146.
Database UniProt. 'Onlinel, Oct. 1, 2000, "Teichoic acid glycosylation protein GtcA" XP002318147.
Database UniProt 'Online!, Feb. 1, 1995, "Hypothetical protein ywcD", XP002318148.

(Continued)

Primary Examiner—Ram R. Shukla
Assistant Examiner—Amanda Shaw
(74) Attorney, Agent, or Firm—Stephen A. Bent; Foley & Lardner LLP

(57) ABSTRACT

An object of the present invention is to provide probes and primers for detecting beer-spoilage lactic acid bacteria with accuracy. The probes and primers for detecting beer-spoilage lactic acid bacteria according to the present invention each comprises a nucleotide sequence consisting of at least 15 nucleotides that hybridizes with the nucleotide sequence of SEQ ID NO: 1 or the complementary sequence thereof.

21 Claims, 1 Drawing Sheet

OTHER PUBLICATIONS

Database EMBL 'Onlinel, Jul. 17, 1991, "A. vinelandii glutamine synthetase (glnA) gene, complete cds", XP002318149.

Thomas A. Tompkins et al., "RAPD-PCR characterization of brewery yeast and beer spoilage bacteria", Journal of the American Society of Brewing Chemists, vol. 54, No. 2, 1996, pp. 91-96, XP009040497.

Database EMBL 'Onlinel, Sep. 6, 2001, "603255791F1 NIH_MGC_97 Homo sapiens cDNA clone Image:5298047 5', mRNA sequence", XP002318150.

Database EMBL 'Onlinel Apr. 4, 2002, "Mus musculus chromosome 13 clone RP24-375M13, Working Draft Sequence, 6 unordered pieces. Entry Deleted from Rel. 81 Dec. 31, 2004". XP002318151.

Database EMBL 'Online! Feb. 23, 2002, "BOMNQO6TF BO_2_3_KB Brassica oleracea genomic clone BONMQ06, DNA sequence", XP002318152.

Database Geneseq 'Online!, May 16, 2002, "Lactococcus lactis protein ykcF", XP002318153.

Database UniProt 'Online! Dec. 1, 2001, "Lin1067 pritein", XP002318145.

Database Geneseq 'Onlinel, Feb. 5, 2002, "Listeria monocytogenes protein #555" XP002318154.

Koji Suzuki et al., 'Biochemical characterization of horA-independent hop resistance mechanism in Lactobacillus brevis, International Journal of Food Microbiology, vol. 76, No. 3, Feb. 8, 2002, pp. 223-230 XP002307887.

Vaughan, E.E., et al., "Identification and characterization of the insertion element IS1070 from Leuconostoc lactis NZ6009." Gene, vol. 155, No. 1, pp. 95-100 (1995).

Patent Abstracts of Japan, JP 11-018780 A (Jan. 26, 1999).

Patent Abstracts of Japan, JP 10-14584 A (Jan. 20, 1998).

Database EMBL 'Online!' Jan. 6, 1995, "Leuconostoc lactic insertion sequence IS1070: IS1070 putative transposase (tnp) gene, complete cds", XP002307344 Database accession No. LL17353 *Abstract.

Database EMBL 'Online!' May 11, 2000, "Neurospora crassa DNA linkage group II BAC clone B208", XP002307888 Database accession No. AL355930 *Abstract.

Database EMBL 'Online!' Feb. 2, 1993, "A. caulinodans NtrY/NtrX DNA sequence", XP002307889, Database accession No. X63841 *Abstract.

Database UniProt 'Online!' Jul. 15, 1998, "Putative glycosyl transferase ykoT (EC 2. -.-.-.).", xpoo2307345 Database accession No. YKOT_BACSU *Abstract.

N. Hayashi et al., "Molecular cloning of a putative divalent-cation transporter gene as a new genetic marker for the identification of Lactobacillus brevis strains capable of growing in beer", Applied Macrobiology and Biotechnology, May 2001, vol. 55, No. 5, pp. 596-603.

Thomas Tompkins et al., "RAPD-PCR characterization of brewery yeast and beer spoilage bacteria", Journal of the American Society of Brewing Chemists. vol. 54, No. 2, 1996, pp. 91-96.

Database EMBL 'Online!', Dec. 7, 2001, "Ralstonia solanacearum GMI1000 chromosome, complete sequence, segment 17/19" XP002307890, Database Accession No. AL646073, *Abstract.

* cited by examiner

POLYNUCLEOTIDE PROBE AND PRIMER FOR DETECTING BEER-CLOUDING LACTIC ACID BACTERIA AND METHOD OF DETECTING BEER-CLOUDING LACTIC ACID BACTERIA

BACKGROUND OF THE INVENTION

1. Field of the Invention

The present invention relates to a method of detecting lactic acid bacteria which cause beer turbidity or cloudiness and affect beer quality. The present invention also relates to a protein specific to lactic acid bacteria which cause beer turbidity or cloudiness and a polynucleotide encoding the protein.

2. Description of the Background Art

Beer is a drink that has limited carbon sources, contains alcohol and carbon dioxide gas, presents low pH and anaerobic conditions, and further contains substances having antimicrobial activity derived from hops such as isohumulone, making it difficult for microbial contamination or microbial growth to occur. However, it is known that when, even under these conditions, beer is contaminated with a certain kind of lactic acid bacteria which belong to genus *Lactobacillus* or genus *Pediococcus*, the bacteria grow and cause beer turbidity or cloudiness to greatly affect the quality of beer. Typical examples of such lactic acid bacteria include *L. brevis*, *P. damnosus* and *L. lindneri* but some other lactic acid bacteria are also confirmed to have such activity. However, it is known that even among lactic acid bacteria that belong to the same species, some strains grow in beer to cause turbidity and cloudiness (hereinafter referred to as "beer-spoilage lactic acid bacteria") while others don't grow (hereinafter referred to as "non-beer-spoilage lactic acid bacteria"). This inconsistency often occurs with strains of *L. brevis* and *P. damnosus*. Therefore, beer-spoilage lactic acid bacteria cannot be directly detected simply by distinguishing the species.

Methods for the detection and distinction of lactic acid bacteria that affect the quality of beer have been studied to date. In a typical method, DNA is extracted from lactic acid bacteria and the presence of a particular gene of beer-spoilage lactic acid bacteria (hereinafter referred to as a "marker") is confirmed by Southern hybridization reaction or the like. In particular today, a method of distinguishing lactic acid bacteria by amplifying a DNA sequence by a PCR (polymerase chain reaction) method using an oligonucleotide as a primer (Japanese Patent Laid-Open Publication No. 141899/1994) is used to distinguish lactic acid bacteria. This method has advantages such that only a small amount of bacterial cells is required for distinction, the operation is simple, and a result can be obtained in a short time.

When this method is used for distinguishing beer-spoilage lactic acid bacterial, its success or failure is most influenced by a marker and a primer sequence constructed based on the marker. Namely, beer-spoilage lactic acid bacteria having a marker and a primer sequence constructed from the marker can easily be detected, but beer-spoilage lactic acid bacteria not having such sequences cannot be detected even if they are present. On the other hand, when non-beer-spoilage lactic acid bacteria having such sequences are present, they are mistakenly detected as beer-spoilage lactic acid bacteria.

In the conventional method for distinguishing beer-spoilage lactic acid bacteria by PCR, an attempt has been made to solve the abovementioned problem by using a 16S ribosomal RNA gene as a marker and constructing a primer based on this marker. The 16S ribosomal RNA gene is a gene essential for sustaining bacterial viability and is highly preservable, but it has a region where the DNA sequence can be different in different organic species, which is called a variable region. This variable region is widely used in classification of organic species, genealogical analysis of evolution, and the like, and similarly for lactic acid bacteria, this gene can be used as a marker to detect and distinguish the abovementioned *L. brevis*, *P. damnosus*, *L. lindneri*, and the like.

However, there are two problems with this method. First, it is highly probable that since the DNA sequence of the primer is associated with a gene which is not directly related to the beer-spoilage ability, beer-spoilage lactic acid bacteria having a certain mutation in this site cannot be detected, even if they are present. The variable region of the 16S ribosomal RNA gene is considered to be vulnerable to mutation and thus beer-spoilage lactic acid bacteria having mutation in a small region of the PCR primer may not be detected even if they are present.

The other problem is that this method, which is essentially for the distinction of organic species, cannot be applicable to distinguish beer-spoilage lactic acid bacteria from non-beer-spoilage lactic acid bacteria, particularly for *L. brevis* and *P. damnosus*, because among lactic acid bacteria that belong to the same species, some strains could be beer-spoilage lactic acid bacteria while others could be non-beer-spoilage lactic acid bacteria, as mentioned above.

Accordingly, there has been a need for a marker gene which detects beer-spoilage lactic acid bacteria more accurately than the 16S ribosomal RNA gene.

An example of the most desirable marker to detect beer-spoilage lactic acid bacteria more accurately than the 16S ribosomal RNA gene is firstly the very causative gene that renders lactic acid bacteria beer-spoilage ability. Further, the next preferable marker is a base sequence which is known to be located in the proximity to the gene that renders lactic acid bacteria beer-spoilage ability.

There have been several reports on genes which are considered to be important for beer-spoilage lactic acid bacteria to acquire the beer-spoilage ability. For example, there is a report on a method of constructing a probe for the distinction of beer-spoilage lactic acid bacteria from a plasmid which is known to grow in lactic acid bacteria which have become resistant to a high hop concentration by gradual acclimatization to a medium containing a high concentration of hops (Japanese Patent Publication No. 3057552).

However, this method has a problem that it does not necessarily reflect the primary difference between beer-spoilage lactic acid bacteria and non-beer-spoilage lactic acid bacteria since the lactic acid bacteria are treated forcefully to acquire the hop resistance.

There are reports on obtaining genes specific to beer-spoilage lactic acid bacteria. For example, as for genes derived from *L. brevis*, horA obtained as a hop resistance gene (Journal of the American Society of Brewing Chemistry, 55, 137-140, 1997) and hita, which is considered to be a gene related to manganese intake (Federation of European Microbiological Societies and Netherlands Society for Microbiology, Abstract of the Sixth Lactic Acid Bacteria Symposium, September 1999), have been reported. Though not quite satisfactorily, these gene are considered to be effective as markers for determining beer-spoilage lactic acid bacteria for *L. brevis*; however, horA erroneously identifies non-beer-spoilage lactic acid bacteria as beer-spoilage lactic acid bacteria at a high frequency for *L. brevis* and neither of the genes can distinguish beer-spoilage lactic acid bacteria for *P. damnosus*. Therefore, there has been a need for a marker for the detection of beer-spoilage lactic acid bacteria which is widely applicable and has a high correlation with the spoilage ability as compared to these previously reported markers.

SUMMARY OF THE INVENTION

An object of the present invention is to provide a method of distinguishing beer-spoilage lactic acid bacteria with improved accuracy and a probe, a primer, a primer pair, and an antibody for use in implementing this method.

Further, another object of the present invention is to provide a protein specific to lactic acid bacteria having beer-spoilage ability, a method of producing said protein, a polynucleotide encoding said protein, a vector carrying said polynucleotide, and a host transformed by said vector.

The present inventor has now succeeded in obtaining a region (SEQ ID NO: 79) which contains a specific gene widely found in beer-spoilage lactic acid bacteria (Example 1). Further, the present inventor has found that beer-spoilage lactic acid bacteria can be distinguished at an extremely high probability when the distinction was carried out by a PCR method using a primer constructed based on this gene (Example 2).

A polynucleotide probe for detecting beer-spoilage lactic acid bacteria according to the present invention comprises a nucleotide sequence consisting of at least 15 nucleotides, which hybridizes with the nucleotide sequence of SEQ ID NO: 1 or the complementary sequence thereof.

A method of detecting beer-spoilage lactic acid bacteria according to the present invention comprises the steps of hybridizing a polynucleotide probe of the present invention with a polynucleotide in a sample and then detecting a hybridization complex.

A polynucleotide primer for use in the detection of beer-spoilage lactic acid bacteria by a nucleic acid amplification reaction according to the present invention comprises a nucleotide sequence consisting of at least 15 nucleotides, which hybridizes with the nucleotide sequence of SEQ ID NO: 1 or the complementary sequence thereof.

A primer pair according to the present invention comprises two kinds of primers of the present invention and can amplify a genomic sequence specific to beer-spoilage lactic acid bacteria by a nucleic acid amplification method.

A method for detecting beer-spoilage lactic acid bacteria according to the present invention comprises the steps of amplifying a polynucleotide in a sample by a nucleic acid amplification reaction using a primer pair of the present invention and then detecting the resulting amplified polynucleotide.

A protein according to the present invention comprises the amino acid sequence of SEQ ID NO: 3, the amino acid sequence of SEQ ID NO: 5, or the amino acid sequence of SEQ ID NO: 7.

Further, a protein according to the present invention is a protein which is obtainable by the steps of culturing a host comprising a recombinant vector carrying a polynucleotide described below and recovering the protein that is an expression product of said polynucleotide.

A polynucleotide according to the present invention encodes the amino acid sequence of SEQ ID NO: 3, the amino acid sequence of SEQ ID NO: 5, or the amino acid sequence of SEQ ID NO: 7.

A recombinant vector according to the present invention carries a polynucleotide of the present invention.

A transformed host according to the present invention comprises a recombinant vector of the present invention.

A method for producing a protein according to the present invention comprises the steps of culturing a host comprising a recombinant vector carrying a polynucleotide of the present invention and recovering the protein that is an expression product of said polynucleotide.

An antibody according to the present invention is against a protein according to the present invention.

A method of detecting beer-spoilage lactic acid bacteria according to the present invention comprises the steps of reacting an antibody according to the present invention with a sample and detecting the antigen-antibody reaction.

DETAILED DESCRIPTION OF THE INVENTION

Polynucleotide Probe

Figure 1:
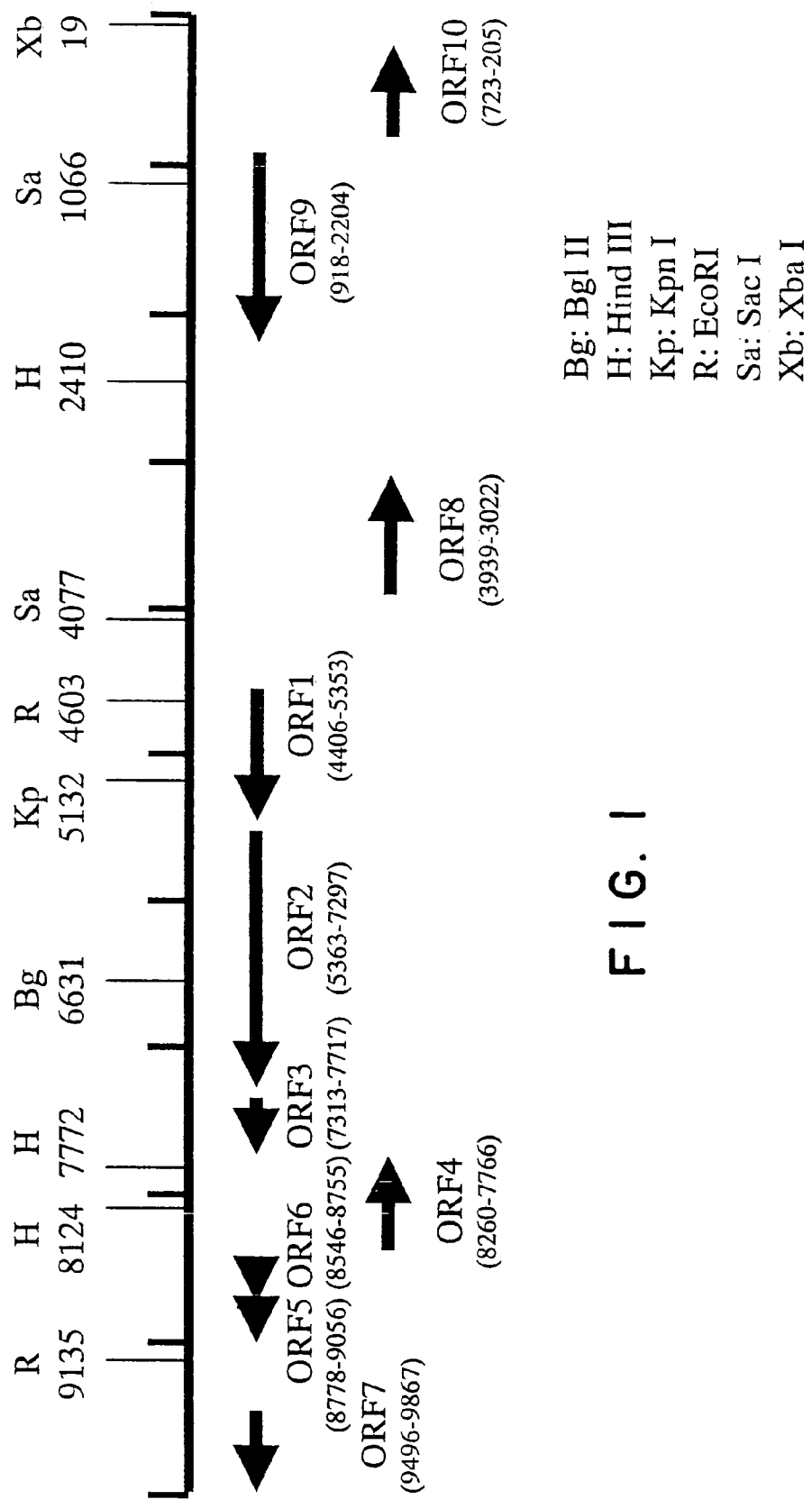
FIG. 1 shows the positions of the open reading frames and the restriction sites in the gene region (SEQ ID NO: 79) specific to beer-spoilage lactic acid bacteria.

As shown in Example 1, the present inventor succeeded in obtaining a gene region specific to beer-spoilage lactic acid bacteria (SEQ ID NO: 79). The obtained region has 10 open reading frames (ORFs) (designated as ORF1 to ORF10; see FIG. 1). In particular, genes of ORF1 to ORF3 form a single operon, and presumably ORF3 is a gene for glycosyltransferase or dolichol phosphate mannose synthetase, and ORF3 is a gene for teichoic acid galactosyltransferase. Accordingly, this operon is considered to be involved in sugar chain synthesis in the cell wall. It has been reported that a particular sugar chain is present in the cell surface layer of beer-spoilage lactic acid bacteria by Yasui et al. (FERM Microbiology Letters, 133, 181-186, 1995) and Tsuchiya et al. (Journal of the American Society of Brewing Chemistry, 58, 89-93, 2000). Further, as shown later in the example, markedly high correlation with beer-spoilage ability was found when detection was carried out using these genes as a marker. Therefore, at least, these three genes are involved in the sugar chain synthesis on the cell surface layer and contribute to the growth of beer-spoilage lactic acid bacteria in beer. In other words, it is highly probable that they are at least a part of causative gene related to the beer-spoilage ability. Accordingly, this operon region is useful as a marker for distinguishing beer-spoilage ability and a polynucleotide probe based on the nucleotide sequence of this region according to the present invention can be used for detecting beer-spoilage lactic acid bacteria.

Further, the present inventor fully studied both sides of the operon region to find out up to which extent the region could be used as a marker for distinguishing beer-spoilage ability and obtained the following results (see Example 2).

(1) When regions ORF1 through ORF4, and ORF8 are each used as a marker, beer-spoilage lactic acid bacteria can be distinguished from non-beer-spoilage lactic acid bacteria at a markedly high frequency for lactic acid bacterial such as *L. brevis* and *P. damnosus*.

(2) When regions ORF9 and ORF10 are each used as a marker, beer-spoilage lactic acid bacteria can be distinguished from non-beer-spoilage lactic acid bacteria at a markedly high frequency for *L. brevis* but not for *P. damnosus*.

(3) Regions ORF5, ORF6 and ORF7 cannot be used for distinguishing beer-spoilage lactic acid bacteria from non-beer-spoilage lactic acid bacteria at least as far as the inventor studied. (However, ORF7 can possibly be used for distinguishing species of lactic acid bacteria.)

Accordingly, a probe according to the present invention can be preferably a probe comprising at least 15 contiguous nucleotides of the nucleotide sequence of SEQ ID NO: 1 or the complementary sequence thereof.

A polynucleotide probe according to the present invention can be preferably a probe comprising at least 15 contiguous nucleotides of the sequence from position 2818 to position 8056 of SEQ ID NO: 1 or the complementary sequence thereof (sequence extending from ORF1 through ORF4 and ORF8; see FIG. 1), more preferably a probe comprising at least 15 contiguous nucleotides of the sequence from position 4202 to position 7513 of SEQ ID NO: 1 or the complementary sequence thereof (sequence extending from ORF1 through ORF3; see FIG. 1), and most preferably a probe comprising at least 15 contiguous nucleotides of the nucleotide sequence of SEQ ID NO: 2 (ORF1), SEQ ID NO: 4 (ORF2), or SEQ ID NO: 6 (ORF3) or the complementary sequence thereof.

A probe comprising at least 15 contiguous nucleotides of any one of SEQ ID NO: 2 (ORF1), SEQ ID NO: 4 (ORF2), and SEQ ID NO: 6 (ORF3) has an advantage that beer-spoilage lactic acid bacteria can be detected without difficulty even if the beer-spoilage lactic acid bacteria having the same ORF sequences but in different order.

A probe according to the present invention can also be a probe which has at least 70%, preferably at least 80%, more preferably at least 90%, most preferably at least 95% homology to the nucleotide sequence comprising 15 contiguous nucleotides of the nucleotide sequence of SEQ ID NO: 1 or the complementary sequence thereof, and hybridizes with a genomic sequence specific to beer-spoilage lactic acid bacteria.

Examples of the "genomic sequence specific to beer-spoilage lactic acid bacteria" include the nucleotide sequence of SEQ ID NO: 1 and a partial sequence thereof, the nucleotide sequence of SEQ ID NO: 2 and a partial sequence thereof, the nucleotide sequence of SEQ ID NO: 4 and a partial sequence thereof, and the nucleotide sequence of SEQ ID NO: 6 and a partial sequence thereof.

In the present invention, the term "hybridize" means to hybridize with a target nucleotide sequence under stringent conditions and not to hybridize with a nucleotide sequence other than the target nucleotide sequence. The stringent conditions can be determined depending on Tm (° C.) of the double strand of a probe sequence (or a primer sequence described below) and a complementary chain thereof, the necessary salt concentration, or the like, and it is a well-known technique to the skilled in the art to set appropriate stringent conditions after selecting a sequence for a probe (for example, see J. Sambrook, E. F. Frisch, T. Maniatis; Molecular Cloning, 2nd edition, Cold Spring Harbor Laboratory, 1988). For example, when hybridization is carried out using a probe consisting of 15 nucleotides under stringent conditions appropriate to this probe (at a temperature slightly lower than the Tm determined by a nucleotide sequence and at an appropriate salt concentration), the hybridization takes place specifically with a sequence complementary to this nucleotide sequence and not with a sequence non-complementary to this nucleotide.

In the present invention, the term "polynucleotide probe" means a probe that is used for means of detecting nucleic acid, such Southern hybridization, Northern hybridization, and colony hybridization.

In the present invention, the term "polynucleotide" includes DNA, RNA, and PNA (peptide nucleic acid).

A polynucleotide probe according to the present invention has at least 15 nucleotides length, more preferably at least 20 nucleotides length.

A polynucleotide probe according to the present invention can be prepared by chemical synthesis of nucleic acid according to an ordinary method such as a phosphite triester method (Hunkapiller, M. et al., Nature, 310, 105, 1984), or by obtaining the whole DNA of beer-spoilage lactic acid bacteria which belong to L. brevis and then appropriately obtaining a DNA fragment containing a target nucleotide sequence based on a nucleotide sequence disclosed in this specification using a PCR method or the like, according to the method described in the Example below.

Method for Detecting Beer-Spoilage Lactic Acid Bacteria Using Polynucleotide Probe A detection method using a polynucleotide probe can be carried out by hybridizing a polynucleotide probe according to the present invention with a nucleic acid sample and then detecting a hybridization complex, namely a nucleotide double strand. In a detection method according to the present invention, the presence of the hybridization complex indicates the presence of beer-spoilage lactic acid bacteria.

In a detection method using a probe, the term "hybridize" means the same as described in the polynucleotide probe section above.

In a detection method using a probe, the probe can be labeled. Examples of the labels include those using radioactivity (e.g., $^{32}P$, $^{14}C$ and $^{35}S$), fluorescence (e.g., FITC and europium), and enzyme reactions, for example, with chemical coloring (e.g., peroxidase and alkaline phosphatase).

Detection of a hybridization complex can be carried out using conventional techniques such as Southern hybridization and colony hybridization (for example, see J. Sambrook, E. F. Frisch, T. Maniatis; Molecular Cloning, 2nd edition, cold Spring Harbor Laboratory, 1989).

A test sample can be a sample suspected to contain beer-spoilage lactic acid bacteria and more specifically, a bacterial colony detected by a microbial examination of beer.

Primer and Primer Pair

A primer and a primer pair according to the present invention each can hybridize with a genomic sequence specific to beer-spoilage lactic acid bacteria. Accordingly, a primer pair according to the present invention can be used for detecting beer-spoilage lactic acid bacteria by a nucleic acid amplification method such as a PCR method.

A primer according to the present invention can preferably be a primer comprising at least 15 contiguous nucleotides of the nucleotide sequence of SEQ ID NO: 1 or the complementary sequence thereof.

In the present invention, the term "primer" means a nucleotide sequence for use in a nucleic acid amplification method such as a PCR method.

In the present invention, the term "primer pair" means a pair of primers for use in a nucleic acid amplification method such as a PCR method.

A primer according to the present invention can comprise at least 15 nucleotides (preferably 15 to 30 nucleotides), preferably at least 20 nucleotides (more preferably 20 to 30 nucleotides).

A primer pair according to the present invention can be selected so that a genomic sequence specific to beer-spoilage lactic acid bacteria can be amplified by a nucleic acid amplification method such as a PCR method. A nucleic acid amplification method is known and the selection of the primer pair in the nucleic acid amplification method will be understood by those skilled in the art. For example, in a PCR method, primers can be selected so that one of the two primers attaches to one chain of a double stranded DNA specific to beer-spoilage lactic acid bacteria, the other primer attaches to the other chain of the double stranded DNA and one primer attaches to an extended chain extended by the other primer.

More specifically, a primer pair can be selected so that one primer comprises at least 15 contiguous nucleotides of the nucleotide sequence of SEQ ID NO: 1 and the other primer comprises at least 15 contiguous nucleotides of the sequence complementary to the nucleotide sequence of SEQ ID NO: 1. Further, since particularly the regions of ORF1, ORF2, ORF3, ORF4, and ORF 8 are considered to be specific to beer-spoilage lactic acid bacteria, a primer can be designed so that these regions can be amplified (see Examples 2 and 3).

Further, a primer pair according to the present invention can be preferably a primer pair in which one primer comprises at least 15 contiguous nucleotides of the nucleotide sequence from position 2818 to position 8056 of SEQ ID NO: 1 (sequence covering ORF1 through ORF 4 and ORF8) and the other primer comprises at least 15 contiguous nucleotides of the sequence complementary to the nucleotide sequence from position 2818 to position 8056 of SEQ ID NO: 1, more preferably a primer pair in which one primer comprises at least 15 contiguous nucleotides of the nucleotide sequence from position 4202 to position 7513 of SEQ ID NO: 1 (sequence covering ORF1 through ORF 3) and the other primer comprises at least 15 contiguous nucleotides of the sequence complementary to the nucleotide sequence from position 4202 to position 7513 of SEQ ID NO: 1, and most preferably a primer pair in which one primer comprises at least 15 contiguous nucleotides of nucleotide sequence of SEQ ID NO: 2, SEQ ID NO: 4, or SEQ ID NO: 6 and the other primer comprises at least 15 contiguous nucleotides of the sequence complementary to the nucleotide sequence of SEQ ID NO: 2, SEQ ID NO: 4, or SEQ ID NO: 6.

A primer pair which amplifies one of the sequences of SEQ ID NO: 2 (ORF1), SEQ ID NO: 4 (ORF2) and SEQ ID NO: 6 (ORF3) or a partial sequence thereof has an advantage that beer-spoilage lactic acid bacteria can be detected without difficulty even if the beer-spoilage lactic acid bacteria having the same ORF sequences but in different order.

A primer according to the present invention can also be a probe which has at least 70%, preferably at least 80%, more preferably at least 90%, most preferably at least 95% homology to the nucleotide sequence comprising 15 contiguous nucleotides of the nucleotide sequence of SEQ ID NO: 1 or the complementary sequence thereof, and hybridizes with a genomic sequence specific to beer-spoilage lactic acid bacteria.

A primer according to the present invention can be chemically synthesized based on a nucleotide sequence disclosed in this specification by an ordinary method such as a phosphite triester method (Hunkapiller, M. et al., Nature, 310, 105, 1984). Primers can be prepared, for example, according to "Bio Experiment Illustrated 3, Virtually Amplifying PCR" (by Hiroki Nakayama, Shujun sha).

Method of Detecting Beer-Spoilage Lactic Acid Bacteria Using Primer Pair

The term "hybridize" in a detection method using a primer pair means the same as described in the polynucleotide probe section above.

As disclosed in the Example described below, the detection of beer-spoilage lactic acid bacteria using a primer pair can be carried out by obtaining DNA from a sample, performing PCR with a primer according to the present invention using this DNA as a template according to an ordinary method, and detecting the presence or absence of amplification of DNA fragments specific to beer-spoilage lactic acid bacteria. The PCR technique itself is well known (for example, see "Bio Experiment Illustrated 3, Virtually Amplifying PCR") and those skilled in the art can carry out a method of the present invention using an appropriate primer. In a detection method using a primer pair according to the present invention, the presence of amplification products indicates the presence of beer-spoilage lactic acid bacteria.

A test sample can be a sample suspected to contain beer-spoilage lactic acid bacteria and more specifically, a bacterial colony detected by a microbial examination of beer.

Protein Specific to Beer-Spoilage Lactic Acid Bacteria and Polynucleotide Encoding the Protein A protein according to the present invention can be an indicator for the presence of beer-spoilage lactic acid bacteria since it is specifically expressed in beer-spoilage lactic acid bacteria. Accordingly, a protein according to the present invention is useful, for example, in preparing an antibody according to the present invention as described below.

A protein according to the present invention include a protein comprising the amino acid sequence of SEQ ID NO: 3 which has one or more modifications and has glucosyltransferase or dolichol phosphate mannose synthetase activity, and a protein comprising the amino acid sequence of SEQ ID NO: 7 which has one or more modifications and has teichoic acid galactosyltransferase activity.

The term "modification" in this specification means substitutions, deletions, additions and insertions. The number of modifications can be, for example, one to several, more specifically one to six. When two or more modifications are present, the type of introduced modifications can be the same or different.

Further, a protein according to the present invention can be specified as a protein which is obtainable by the steps of culturing a host comprising a recombinant vector carrying a polynucleotide according to the present invention and collecting the protein that is an expression product of said polynucleotide.

A polynucleotide according to the present invention encodes a protein specific to beer-spoilage lactic acid bacteria and is thus useful for producing a protein according to the present invention using gene recombination technology, as described below.

A polynucleotide according to the present invention can be a chemically synthesized DNA or naturally occurring DNA (derived from chromosomes or plasmids).

In obtaining a polynucleotide according to the present invention, a DNA fragment having the sequence of SEQ ID NO: 2, SEQ ID NO: 4, or SEQ ID NO: 6 is obtainable, for example, by obtaining the whole DNA of beer-spoilage lactic acid bacteria which belong to L. brevis, appropriately constructing a primer based on a nucleotide sequence disclosed in this specification so as to obtain a DNA fragment containing the target nucleotide sequence, and then amplifying the DNA fragment by a PCR method, according to the method described in the Example below, or alternatively, a polynucleotide can be prepared by nucleic acid chemical synthesis according to an ordinary method such as the phosphite triester method (Hunkapiller, M. et al., Nature, 310, 105, 1984). DNA having a nucleotide sequence of a degenerate sequence of the base sequence of SEQ ID NO: 2, SEQ ID NO: 4, or SEQ ID NO: 6 is obtainable by nucleic acid chemical synthesis based on an amino acid sequence disclosed in this specification.

A DNA sequence thus obtained can be confirmed by analysis according to a Maxam Gilbert method (for example, described in Maxam, A. M. and W. Gilbert, Proc. Natl. Acad. Sci. USA, 74, 560, 1977) or a Sanger method (for example, described in Sanger, F. and A. R. Coulson, J. Mol. Biol., 94, 441, 1975; Sanger, F., S, Nicklen and A. R. Coulson, Proc. Natl. Acad. Sci. USA, 74, 5463, 1977).

Recombinant Vector and Transformant

A recombinant vector according to the present invention can be constructed by incorporating a polynucleotide according to the present invention into a vector which is replicable in a host and carries a detectable marker gene, using an ordinary genetic engineering technique.

A recombinant vector according to the present invention can be produced according to a technique conventionally used for vector construction. More specifically, when a microorganism *Escherichia coli* is used as a host, for example, plasmid pUC119 (Takara Shuzo Co. Ltd.) and phagemid pBluescript II (Stratagene) can be used. When a yeast is used as a host, plasmid pYES2 (Invitrogen Corp.) can be used. When a mammalian cell is used as a host, plasmids such as pRC/RSV and pSRC/CMV (Invitrogen Corp.), a vector containing self-replication origin derived from viruses, such as EB virus plasmid Prep4, and pCEP4 (Invitrogen Corp.), can be used. When an insect cell is used as a host, an insect virus such as baculovirus can be used. When DNA is incorporated into a virus such as baculovirus, a transfer vector containing a base sequence homologous to the genome of the virus to be used can be used. Examples of such a transfer vector include plasmids such as pBacPAK8 and pAcUW31 commercially available from Clontech. When a polynucleotide according to the present invention is inserted into a transfer vector and the transfer vector and a virus genome are simultaneously introduced into a host, homologous recombination takes place between the transfer vector and the virus genome, yielding a virus in which the polynucleotide of the present invention is incorporated into the genome.

A vector with which a protein according to the present invention can be expressed in a host can be constructed by operably linking a polynucleotide according to the present invention to regulatory sequences (for example, a promoter sequence and a terminator sequence) operable in the host, and incorporating the product into a vector.

In the present specification, the expression "operably link" means that regulatory sequences are linked to a polynucleotide according to the present invention so that the expression takes place under the control of the regulatory sequences in a host into which the polynucleotide according to the present invention is introduced. Generally, a promoter can be linked to the upstream of the gene and a terminator can be linked to the downstream of the gene.

A promoter to be used is not particularly limited as long as it exhibits promoter activity in a host to be transformed. For example, an adenovirus (Ad) early or late promoter, a Rous sarcoma virus (RSV) promoter, a cytomegalovirus (CMV) promoter, a simian virus (SV40) early or late promoter, a mouse mammalian tumor virus (MMTV) promoter, a thymidine kinase (tk) gene promoter of herpes simplex virus (HSV) can be used when an animal cell or fission yeast is used as a host cell; a ADH1 or GAL1 promoter can be used for a budding yeast; and the baculovirus polyhedron promoter or *Drosophila* metallothionein promoter can be used for an insect cell.

When a vector already carrying a promoter that functions in a host is used, a promoter contained in the vector can be operably linked to a polynucleotide according to the present invention.

For example, in plasmids pRC/RSV, pRC/CMV and the like, a cloning site is located downstream of a promoter operable in an animal cell, and thus a protein according to the present invention can be expressed by inserting a polynucleotide according to the present invention into the cloning site and then introducing the plasmid into the animal cell. Since the SV40 autonomous replication origin (ori) is already incorporated into these plasmids, the number of copies of such plasmids in a cell greatly increases when these plasmids are introduced into a culture cell transformed with an ori(−) SV40 genome, such as a COS cell, which can result in mass expression of the polynucleotide according to the present invention incorporated into said plasmids. Further, plasmid pYES2 for budding yeast has the GAL1 promoter and thus a vector with which a protein according to the present invention can be massively expressed in a budding yeast, such as INVSc1 (Invitrogen Corp.), can be constructed by inserting a DNA according to the present invention downstream of the GALL promoter of this plasmid or a derivative thereof.

A recombinant vector according to the present invention can be further linked to a marker gene to select transformants.

Further, a polynucleotide encoding an amino acid sequence of another protein or a part thereof at the 5' or 3' site of the polynucleotide according to the present invention can be linked in frame to a recombinant vector according to the present invention directly or via a polynucleotide encoding an amino acid sequence corresponding to a cleavage site peculiar to a specific protease. The amino acid sequence of another protein or a part thereof may have a signal peptide for secretion at its N terminal and in such a case, ligation to the 5' site is preferable.

A recombinant vector according to the present invention can be introduced into a host according to an ordinary method suitable for the host to be transformed.

For example, when *E. coli* is used as a host, a calcium chloride method or an electroporation method can be used as described in Molecular Cloning, J. Sambrook et al., Cold Spring Harbor (1989) and the like. When a yeast cell is used as a host, a vector can be introduced, for example, using a Yeast Transformation Kit (Invitrogen Corp.) according to the lithium method. When a mammalian cell, insect cell, or the like is used as a host, a calcium phosphate method, a DEAE dextran method, an electroporation method, a lipofection method, or the like can be used. When a virus is used as a vector, the virus genome can be introduced into a host by using any of the abovementioned ordinary method for gene introduction or by infecting a host with a virus particle carrying the virus genome.

Transformants can be selected by a method appropriate to the nature of a marker gene contained in an introduced recombinant vector according to the present invention.

For example, when the marker gene is a tolerance gene for a drug which exhibits cytotoxic activity, a cell into which a recombinant vector according to the present invention is introduced can be cultured using a medium supplemented with this drug. Examples of a combination of such drug resistance gene and selectable drug include a neomycin resistance gene and neomycin, a hygromycin resistance gene and hygromycin, and a blasticidin S resistance gene and blasticidin S. Further, when the marker gene is a gene complementing nutritional requirement of a host, a cell into which a recombinant vector according to the present invention is introduced can be cultured using a minimal medium without the corresponding nutrient. In order to obtain a transformant in which a gene according to the present invention is incorporated into the host chromosome, for example, a recombinant vector according to the present invention is linearized by digesting with a restriction enzyme or the like, after which the resulting fragment is introduced into the host cell by the abovementioned method, the resulting cell is cultured generally for several weeks, and then the transformant of interest can be selected using a detection marker introduced as an indicator. For example, a recombinant vector according to the present invention having a selectable drug resistance gene as mentioned above as a marker gene is introduced into a host by the abovementioned method, and then cultivation by passage is carried out on a medium supplemented with the selectable drug for several weeks or longer, after which selectable drug resistance clones survived as a colony were sucked up by a pipette and purified, and thus the transformant in which the gene according to the present invention is incorporated into the host chromosome can be obtained. The transformant thus obtained can be stored frozen and revived for use when needed, so that the trouble of constructing the transformant can be avoided and the function of the transformant can be maintained consistently, which makes it advantageous as compared to a strain into which a gene is temporarily incorporated.

A protein according to the present invention can be produced by culturing a transformed host according to the present invention and collecting the protein according to the present invention from the resulting culture.

A protein missing one or more residues at the N terminal and/or C terminal ends due to processing or the like in a host can also be satisfactorily used as an antigen to obtain an antibody according to the present invention. Further, as mentioned in the section of recombinant vector and host, when a DNA encoding an amino acid sequence of another protein or a part thereof can be linked in frame to a recombinant vector according to the present invention at the 5' site or 3' site of the gene according to the present invention directly or via a DNA encoding an amino acid sequence corresponding to a cleavage site specific to a specified protease, a protein according to the present invention is expressed as a fusion protein with the other protein or the part thereof, which is also included in the protein of the present invention.

When a microorganism is used as a host, it can be cultured using any kind of medium appropriately containing carbon sources, nitrogen sources, organic salts, inorganic salts, and the like ordinarily used for cultivation of this microorganism. The cultivation is carried out according to an ordinary culture method for microorganisms, such as solid culture and liquid culture including culture with stirring (e.g., test tube shake culture, reciprocating shake culture, and jar fermenter culture) and static culture (e.g., tank culture). The culture temperature can be appropriately selected within a range suitable for the microorganisms. For example, cultivation can be carried out in a medium at pH about 6 to about 8 at a culture temperature of about 15° C. to about 40° C. The cultivation time can be determined according to the culture conditions; however, it can generally be about 1 day to about 5 days.

When an animal cell is used as a host, it can be cultured using a medium ordinarily used for this animal cell. For example, cultivation can be carried out at 37° C. using a medium such as a DMEM medium supplemented with 10% v/v FBS in the presence of 5% v/v $CO_2$, changing the medium every several days. When the cells are grown to be confluent, they are dispersed into individual cells using an about 0.25% w/v trypsin PBS solution, after diluting several times, the culture is inoculated into a fresh culture vessel and the cultivation is continued until the cells grow up to a targeted amount to recover the cells. By carrying out passage culture in this way, the scale of the culture can be expanded to a desired size.

Similarly, when an insect cell is used as a host, cells can be obtained by passage culture, for example, at 25° C. to 35° C. in a medium for insect cells, such as Grace's medium supplemented with 10% v/v FBS and 2% w/v yeastolate. However, when cells that are easy to come off from a culture vessel, such as an Sf21 cell, are used as hosts, the passage can be preferably carried out by dispersing the cells by pipetting but not with a trypsin solution. Further, when a transformed cell containing a virus vector such as baculovirus vector is used, it is preferable to terminate the cultivation before grown cells die off due to cytoplasmic effect, for example, 72 hours after the start of cultivation.

After cultivation, a protein according to the present invention can be purified and isolated using any known isolation and purification procedure. For example, when a protein according to the present invention is produced intracellularly, this protein can be purified by the steps of collecting cells by centrifugation or the like after cultivation, suspending the cells in an ordinary buffer such as a buffer solution comprising 20 mM HEPES, pH 7, 1 mM EDTA, 1 mM DTT, and 0.5 mM PMSF to subsequently disrupt the cells using a polytron, ultrasonicator, Downs homogenizer, or the like, and recovering the supernatant fraction by ultra-centrifuging the resulting suspension at dozens of thousands ×g for several score minutes to about 1 hour to obtain a fraction containing the target protein according to the present invention.

Further, when a protein according to the present invention is secreted in a medium, a fraction containing the protein according to the present invention can be obtained as a supernatant fraction by centrifugation after cultivation. The supernatant fraction thus obtained is purified using an appropriate combination of purification procedures such as salting out, solvent precipitation, dialysis, ultrafiltration, gel electrophoresis, ion exchange chromatography, gel filtration chromatography, reverse chromatography, and affinity chromatography to recover the purified protein according to the present invention.

Antibody and Method of Detecting Beer-Spoilage Lactic Acid Bacteria Using the Antibody An antibody according to the present invention can recognize a protein specific to beer-spoilage lactic acid bacteria. Accordingly, an antibody according to the present invention can be used for detecting beer-spoilage lactic acid bacteria by antibody-antigen reaction.

An antibody according to the present invention includes both polyclonal antibody and monoclonal antibody. Since the technology for antibody construction is well known, anyone skilled in the art can readily prepare either polyclonal or monoclonal antibody by an ordinary method using a protein according to the present invention as an immunogen.

For example, an antibody according to the present invention can be obtained by administering a protein according to the present invention as an antigen with an adjuvant or the like to mammals, birds, or the like generally used for antibody production, including rabbits, mice, rats, goats, sheep, chickens, hamsters, horses, and guinea-pigs, and then obtaining an antiserum from the animals. The antiserum can be used as it is, or if necessary, it can be further fractionated and purified as described below to obtain a polyclonal antibody. For monoclonal antibody production, for example, a mouse is used as the abovementioned mammal, the spleen of the immunized mouse is extracted, cell fusion is carried out between a lymphocyte prepared from this spleen and a mouse myeloma cell (for example, p3×63 6.5.3 ATCC No. CRL-1580) using polyethylene glycol 1500 (Behringer), and then the resulting fusion cells were screened for positive strains by using a limit dilution method to obtain a hybridoma which produces the target antibody (see C. Milstein & G. Kohler, Nature, 256, 497, 1975). Further, an antibody molecule expressed by means of genetic engineering can be obtained by cloning an antibody gene or a part thereof from the hybridoma cell expressing the antibody.

An antibody is purified from a material containing the antibody thus obtained, namely an antiserum or a culture supernatant of hybridoma cells, by a purification procedure comprising a combination of one or more steps generally used for protein purification (for example, affinity chromatography such as protein A affinity chromatography, protein G affinity chromatography, Avid gel chromatography, and anti-immunoglobulin immobilized gel chromatography, cation-exchange chromatography, anion-exchange chromatography, lectin affinity chromatography, pigment adsorption chromatography, hydrophobic alternate chromatography, gel permeation chromatography, reverse-phase chromatography, hydroxyapatite chromatography, fluoroapatite chromatography, metal chelating chromatography, isoelectric point chromatography, preparatory electrophoresis, and isoelectric point electrophoresis). Further, alternatively, an antigen affinity purification method can be used, in which a gel carrier or a membrane to which a protein according to the present invention is chemically bonded is prepared, a material containing an antibody is added thereto, and the adsorbed antibody of interest is eluted and recovered under appropriate conditions.

Antibody-antigen reaction can be detected according to a known method, for example, as follows. Cells of target lactic acid bacteria are suspended in a solution containing 40 mM Tris-HCl (pH 7.5), 1 mM EDTA, and 150 mM NaCl, and then completely disrupted by vigorously stirring with a sufficient amount of glass beads for several minutes. SDS is added thereto at the final concentration of 0.1% and the suspension is stirred again and then centrifuged to recover the supernatant fraction. The antibody or a Fab' fragment derived from the antibody is labeled by the linking of a labeling enzyme, such as horseradish peroxidase, a fluorescent substance, biotin, a radioactive isotope or the like, and mixed with the cellular extract of the target lactic acid bacteria to sufficiently bond the antibody to the antigen, after which excessive labeled antibody is removed by washing, and beer-spoilage lactic acid bacteria can be detected by measuring, for example, the activity of the enzyme with which the antibody is labeled. Various methods for such detection, such as an enzyme-linked immunosorbent assay (ELISA) method, a Western blot analysis method, and a radioimmunoassay method, are known and detailed procedures can be found, for example, in Antibodies: A Laboratory Manual by Ed Harlow and David Lane, Cold Spring Harbor Laboratory, 1988.

EXAMPLE

The present invention is further illustrated by the following examples that are not intended to limit the scope of the invention.

Example 1

Obtaining Beer-Spoilage Lactic Acid Bacteria Gene

Cells of *L. brevis*, 3 strains of beer-spoilage lactic acid bacteria and 2 strains of non-beer-spoilage lactic acid bacteria, were cultured statically in 100 ml of MRS medium (Oxoid) to stationary phase and grown cells were recovered, after which the whole DNA was obtained from the cells by the method of Douglas et al. (Applied and Environmental Microbiology, 46, 549-552, 1983). The final DNA concentration was adjusted to about 10 mg/ml to 20 mg/ml and random polymorphic DNA PCR (RAPD PCR) (Nucleic Acid Research, 22, 6531-6535, 1990) was carried out using a 2 ml portion of this DNA as a template. Namely, PCR was performed using 540 kinds of primers from Kit AA to AZ of Operon 10-mer Kits (Operon), i.e., primers for genetic mapping comprising random 10-mer synthetic DNAs. A 20 ml portion of each primer was used at a concentration of 20 mM and a reaction solution was prepared in a total volume of 50 ml. A PCR reaction reagent used was a Takara Ex Taq kit from Takara Shuzo Co., Ltd. and a reaction apparatus used was Gene Amp PCR System 9600 from Perkin Elmer. The reaction program was 45 cycles at 94° C. for 1 minute, at 36° C. for 1 minute, and at 72° C. for 2 minutes. After the reaction was completed, the reaction solution was subjected to electrophoresis with 1% agarose gel, the resulting gel was stained with an ethidium bromide solution, and then amplified bands were analyzed to select primers that recognized a gene specific to beer-spoilage lactic acid bacteria, namely, primers that generated bands having a common size for the template DNAs from the 3 strains of beer-spoilage lactic acid bacteria but did not generate bands having a common size for the template DNAs from the 2 strains of non-beer-spoilage lactic acid bacteria, among the abovementioned 540 primers. Further, PCR was performed in the same way with the primers thus primarily selected, using DNAs extracted from 12 strains of beer-spoilage lactic acid bacteria and 8 strains of non-beer-spoilage lactic acid bacteria as a template DNA to more closely select primers which generate bands specific to beer-spoilage lactic acid bacteria.

Base sequences of the finally selected primers were as follows:

OPAT 07 5'-ACTGCGACCA-3' (SEQ ID NO: 8)

OPAR 12 5'-GGATCGTCGG-3' (SEQ ID NO: 9)

OPAX 05 5'-AGTGCACACC-3' (SEQ ID NO: 10)

Next, bands specific to beer-spoilage lactic acid bacteria, which were generated by the abovementioned PCR, were extracted from the agarose gel, recovered using a Mag Extractor PCR and Gel Clean Up kit from Toyobo Co., Ltd, and then cloned into the pCRII vector from Invitrogen Corp.

Base sequences of the bands specific to beer-spoilage lactic acid bacteria thus cloned were determined, which revealed mutually common sequences. It was confirmed that the regions amplified by three different primers were actually a single region on a chromosome.

Accordingly, the whole DNA was prepared from beer-spoilage lactic acid bacteria, *L. brevis* strain L50, using the method of Douglas et al. (Applied and Environmental Microbiology, 46, 549-552, 1983) and this DNA was partially digested with restriction enzyme MboI, after which fragments of 15 to 20 kb were recovered and ligated to the cosmid vector pJB8 to transform *E. coli* DH1 and thus a genomic library was completed. Screening of this genomic library was carried out using a band amplified with the abovementioned OPAT 07 primer as a probe to obtain a DNA fragment having the restriction map shown in FIG. 1. The base sequence of this fragment was determined (SEQ ID NO: 79). Positions of ORF1 through ORF10 in the nucleotide sequence of SEQ ID NO: 79 are as follows:

ORF1: from position 4406 to 5353

ORF2: from position 5363 to 7297

ORF3: from position 7313 to 7717

ORF4: from position 8260 to 7766

ORF5: from position 8778 to 9056

ORF6: from position 8546 to 8755

ORF7: from position 9496 to 9867

ORF8: from position 3939 to 3022

ORF9: from position 918 to 2204

ORF10: from position 723 to 205

Functions of the ORFs found in the abovementioned base sequences were estimated by comparison with a DNA sequence database such as GENBANK. Results are as follows:

ORF1: This frame represents 315 amino acids (SEQ ID NO: 3) and presumably encodes a protein having the function of glucosyltransferase or dolichol phosphate mannose synthetase since it shows 69% homology to a protein of estimated molecular mass of 38.5 kDa which is analogous to dolichol mannose synthetase of Bacillus subtilis.

ORF2: This frame represents 644 amino acids (SEQ ID NO: 5) and shows no homology to any protein in the database used for comparison.

ORF3: This frame represents 134 amino acids (SEQ ID NO: 7) and presumably encodes a protein having the function of a teichoic acid galactosyltransferase since it shows 63% homology to Listeria monocytogenes gtcA, or teichoic acid glycosylated protein.

ORF4: This frame represents 176 amino acids and presumably encodes a protein having the function of a nicking enzyme since it has 86% homology to Lactococcus lactis traA.

ORF5: This frame represents 69 amino acids, which shows 76% homology to a predicted protein ORF0004 of Lactococcus lactis plasmid pMRC01 (Molecular Micro Biology, 4, 1029-1038, 1998).

ORF6: This frame represents 92 amino acids, which shows 77% homology to a predicted protein ORF0003 of Lactococcus lactis plasmid pMRC01 (Molecular Micro Biology, 4, 1029-1038, 1998).

ORF7: This frame represents 123 amino acids and presumably encodes a protein having the function of a transposase since it has 62% homology to OrfA of Caulobacter crescentus IS298.

ORF8: This frame represents 305 amino acids and presumably encodes a protein having the function of a transposase since it shows 62% homology to a predicted transposase of Leuconostoc lactis IS1070.

ORF9: This frame represents 428 amino acids and shows no homology to any protein in the database used for comparison.

ORF10: It represents 172 amino acids and presumably encodes a protein having the function of a transcription regulatory factor since it has 49% homology to Lactococcus lactis yxcB.

Among them, ORF1, ORF2, and ORF3 presumably relate to some sugar chain synthesis since these three ORFs are present within a single operon.

Example 2

Distinction of Beer-Spoilage Lactic Acid Bacteria by PCR

The following primers were designed from each ORF disclosed in FIG. 1:

ORF1-1 5'-GTCAGCGTGCCGACATCCTG-3' (SEQ ID NO: 11)

ORF1-2 5'-TGTATTCACCAATCACCCCG-3' (SEQ ID NO: 12)

ORF2-1 5'-GCCCCGACTTGACCATTTGT-3' (SEQ ID NO: 13)

ORF2-2 5'-TTAGCGGGTGAGCAGCGAGC-3' (SEQ ID NO: 14)

ORF3-1 5'-ACAGCCTTGCGCTACCTGAT-3' (SEQ ID NO: 15)

ORF3-2 5'-TTCACAATCAGCGGCGAACC-3' (SEQ ID NO: 16)

ORF4-1 5'-TGAGTTTTAGTAATATTAGT-3' (SEQ ID NO: 17)

ORF4-2 5'-AGCCAAGCTTGATGCCGGCA-3' (SEQ ID NO: 18)

ORF5-1 5'-AAAGTAACTTAGAAAAACAA-3' (SEQ ID NO: 19)

ORF5-2 5'-ATGATCTACGGACTTTACCT-3' (SEQ ID NO: 20)

ORF6-1 5'-TCAATATGAAAAACTAGTCGAGCAG-3' (SEQ ID NO: 21)

ORF6-2 5'-TTATGGACGTTAACATAGTCAGCA-3' (SEQ ID NO: 22)

ORF7-1 5'-GGAAGATGCTCAGTGGGACCGAATC-3' (SEQ ID NO: 23)

ORF7-2 5'-GCCTTTTGATGCGCTCGAACGAT-3' (SEQ ID NO: 24)

ORF8-1 5'-TCACAGAAAGATTAAGTCGGCAACA-3' (SEQ ID NO: 25)

ORF8-2 5'-TCTAATTCTTTGGCGCTAACCGTC-3' (SEQ ID NO: 26)

ORF9-1 5'-AATTGAAAGTAAGTTGCGAAAGAAA-3' (SEQ ID NO: 27)

ORF9-2 5'-GGCGAACCGTGAACAAATAG-3' (SEQ ID NO: 28)

ORF10-1 5'-TACAATTAGTAAGACAACAGGGATT-3' (SEQ ID NO: 29)

ORF10-2 5'-TCAGGCAATTCTTGTTCATC-3' (SEQ ID NO: 30)

Cells of L. brevis, P. damnosus and a single species of lactic acid bacteria, for which an exact taxonomic species name was unknown, as shown in Tables 1, 2 and 3 were cultured and the whole DNAs were obtained by the method of Douglas et al. (Applied and Environmental Microbiology, 46, 549-552, 1983). PCR was carried out with a primer corresponding to each of the abovementioned ORFs using about 0.1 mg of each of these DNAs as a template DNA. A reaction reagent used was a Takara Ex Taq kit from Takara Shuzo Co., Ltd. and a reaction apparatus used was Gene Amp PCR System 9600 from Perkin Elmer. The reaction program was 25 cycles at 94° C. for 30 seconds, at 60° C. for 30 seconds, and at 72° C. for 1 minute. After the reaction was completed, the reaction solution was subjected to electrophoresis with 1.5% agarose gel to examine the presence or absence of a band specific to beer-spoilage lactic acid bacteria. Further, primers were synthesized according to hita and horA genes, which had been reported as a marker gene for distinguishing beer-spoilage lactic acid bacteria prior to the present invention, and used in a similar experiment to compare results. The results are shown in Tables 1, 2 and 3.

TABLE 1

Determination test for beer-spoilage bacteria for *Lactobacillus brevis* strains

| Strains | Beer-spoilage ability | ORF1-1, 2 primer | ORF2-1, 2 primer | ORF3-1, 2 primer | ORF4-1, 2 primer | ORF5-1, 2 primer | ORF6-1, 2 primer | ORF7-1, 2 primer | ORF8-1, 2 primer | ORF9-1, 2 primer | ORF10-1, 2 primer | hitA-1, 2 primer | horA-1, 2 primer |
|---|---|---|---|---|---|---|---|---|---|---|---|---|---|
| L42 | − | − | − | − | − | + | + | + | − | − | − | − | + |
| L52 | − | − | − | − | − | + | + | + | − | − | − | − | + |
| L57 | − | − | − | − | − | + | + | + | − | − | − | − | + |
| L62 | − | − | − | − | − | + | + | + | − | − | − | − | + |
| L107 | − | − | − | − | − | + | + | − | − | − | − | − | + |
| H10 | − | − | − | − | − | − | − | + | − | − | − | − | + |
| H14 | − | − | − | − | − | − | − | + | − | − | − | − | + |
| L37 | + | + | + | + | + | + | + | + | + | + | + | + | + |
| L38 | + | + | + | + | + | + | + | + | + | + | + | + | + |
| L40 | + | + | + | + | + | + | + | + | + | + | + | + | + |
| L41 | + | + | + | + | + | + | + | + | + | + | + | + | + |
| L43 | + | + | + | + | + | + | + | + | + | + | + | + | + |
| L45 | + | + | + | + | + | + | + | + | + | + | + | + | + |
| L46 | + | + | + | + | + | + | + | + | + | + | + | + | + |
| L48 | + | + | + | + | + | + | + | + | + | + | + | + | + |
| L49 | + | + | + | + | + | + | + | + | + | + | + | + | + |
| L50 | + | + | + | + | + | + | + | + | + | + | + | + | + |
| L53 | + | + | + | + | + | + | + | + | + | + | + | + | + |
| L58 | + | + | + | + | + | + | + | + | + | + | + | + | + |

TABLE 2

Determination test for beer-spoilage bacteria for *Pediococcus damnosus* strains

| Strains | Beer-spoilage ability | ORF1-1, 2 primer | ORF2-1, 2 primer | ORF3-1, 2 primer | ORF4-1, 2 primer | ORF5-1, 2 primer | ORF6-1, 2 primer | ORF7-1, 2 primer | ORF8-1, 2 primer | ORF9-1, 2 primer | ORF10-1, 2 primer | hitA-1, 2 primer | horA-1, 2 primer |
|---|---|---|---|---|---|---|---|---|---|---|---|---|---|
| B27 | − | − | − | − | − | + | − | − | − | + | + | + | + |
| TB6 | − | − | − | − | − | + | − | − | − | + | + | + | + |
| TB23 | − | − | − | − | − | + | + | − | − | + | − | + | + |
| TB25 | − | − | − | − | − | + | + | − | − | + | + | + | + |
| TB30 | − | − | − | − | − | + | + | − | − | + | + | + | + |
| B2 | + | + | + | + | + | + | + | − | + | + | + | + | + |
| B3 | + | + | + | + | + | + | + | − | + | + | + | + | + |
| B4 | + | + | + | + | + | + | + | − | + | + | + | + | + |
| B11 | + | + | + | + | + | + | + | − | + | + | + | + | + |
| B13 | + | + | + | + | + | + | + | − | + | + | + | + | + |
| B15 | + | + | + | + | + | + | + | − | + | + | + | + | + |
| B16 | + | + | + | + | + | + | + | − | + | + | + | + | + |
| B20 | + | + | + | + | + | + | + | − | + | + | + | + | + |
| B22 | + | + | + | + | + | + | + | − | + | + | + | + | + |
| B23 | + | + | + | + | + | + | + | − | + | + | + | + | + |
| TB2 | + | + | + | + | + | + | + | − | + | + | + | + | + |
| PD1 | + | + | + | + | + | + | + | − | + | + | + | + | + |
| PD2 | + | + | + | + | + | + | + | − | + | + | + | + | + |

TABLE 3

Determination test for beer-spoilage bacteria for strains of lactic acid bacteria for which species name is unknown

| Strains | Beer-spoilage ability | ORF1-1, 2 primer | ORF2-1, 2 primer | ORF3-1, 2 primer | ORF4-1, 2 primer | ORF5-1, 2 primer | ORF6-1, 2 primer | ORF7-1, 2 primer | ORF8-1, 2 primer | ORF9-1, 2 primer | ORF10-1, 2 primer | hitA-1, 2 primer | horA-1, 2 primer |
|---|---|---|---|---|---|---|---|---|---|---|---|---|---|
| 4 | − | − | − | − | − | + | + | − | − | − | − | − | − |
| 5 | − | − | − | − | − | + | + | − | − | − | − | − | − |
| 6 | − | − | − | − | − | + | + | − | − | − | − | − | − |
| 7 | − | + | + | + | + | + | + | − | + | + | + | − | − |
| 9 | − | − | − | − | − | + | + | − | − | − | − | − | − |
| 10 | − | − | − | − | − | + | + | − | − | − | − | − | − |
| 12 | − | − | − | − | − | + | + | − | − | − | − | − | − |
| 15 | − | − | − | − | − | + | + | − | − | − | − | − | − |
| 19 | − | − | − | − | − | + | + | − | − | − | − | − | − |
| 8 | + | + | + | + | + | + | + | − | + | + | + | − | − |
| 11 | + | − | − | − | − | + | + | − | − | − | − | − | − |
| 16 | + | + | + | + | + | + | + | − | + | + | + | − | − |
| 21 | + | + | + | + | + | + | + | − | + | + | + | − | − |

TABLE 3-continued

Determination test for beer-spoilage bacteria for strains of lactic acid bacteria for which species name is unknown

| Strains | Beer-spoilage ability | ORF1-1, 2 primer | ORF2-1, 2 primer | ORF3-1, 2 primer | ORF4-1, 2 primer | ORF5-1, 2 primer | ORF6-1, 2 primer | ORF7-1, 2 primer | ORF8-1, 2 primer | ORF9-1, 2 primer | ORF10-1, 2 primer | hitA-1, 2 primer | horA-1, 2 primer |
|---|---|---|---|---|---|---|---|---|---|---|---|---|---|
| 22 | + | + | + | + | + | + | + | − | + | + | + | − | − |
| 23 | + | + | + | + | + | + | + | − | + | + | + | − | − |

As a result, as shown in Tables, when the operon comprising ORF1, ORF2 and ORF3 was used as a marker, beer-spoilage lactic acid bacteria could be distinguished at a markedly high frequency for both *L. brevis* and *P. damnosus*. Further, many beer-spoilage lactic acid bacteria could be distinguished for the strains of taxonomically unknown single species lactic acid bacteria, although the frequency of the distinction was slightly low.

Next, when ORF4 and ORF8 each neighboring this operon region were used as a marker, beer-spoilage lactic acid bacteria could be distinguished at completely the same frequency as with the genes in the operon.

On the other hand, when the horA gene was used as a marker, the bands were detected for all of the *L. brevis* and *P. damnosus* strains tested, while absolutely no band was detected for the strains of taxonomically unknown single species lactic acid bacteria.

When the hitA gene was used as a marker, beer-spoilage lactic acid bacteria could be distinguished for *L. brevis* at completely the same frequency as with ORF1 through ORF4 and ORF8; however, the bands were detected for all strains of *P. damnosus* while absolutely no band was detected for the strains of taxonomically unknown single species lactic acid bacteria.

From the results above, it was revealed that the genes of ORF1 through ORF4 and ORF8 disclosed by the present invention were superior to the previously reported genes as a marker for beer-spoilage lactic acid bacteria.

Further, when ORF9 and ORF10 were used as a marker, beer-spoilage lactic acid bacteria could also be distinguished at a markedly high frequency if limited solely to the strains of *L. brevis*. When ORF5, ORF6 and ORF7 were used as a marker, no beer-spoilage lactic acid bacteria could be distinguished.

Example 3

Construction of Oligonucleotides for Other Primers and Probes for Regions Highly Specific to Beer-Spoilage Lactic Acid Bacteria Primer pairs were designed based on the base sequences of regions of ORF1, ORF2, ORF3, ORF4 and ORF8 having particularly high specificity to beer-spoilage lactic acid bacteria. If necessary, primer pairs can be designed using software for designing primers (for example, OLIGO primer analysis software ver. 6.0, National Biosciences, Inc.) or the like.

Oligonucleotides were prepared by chemical synthesis and the obtained primer pairs were used for a PCR method. PCR primer pairs for each ORF region and hybridization conditions are as follows. These oligonucleotides can be used singly as a probe.

(1) ORF1-Related PCR Primers

5'-TTACTGGCCGTTGAAG-3' (SEQ ID NO: 31)

5'-TGAGCTTGCCGATGT-3' (SEQ ID NO: 32)
Conditions for PCR reaction are 25 cycles of 30 seconds at 94° C., 30 seconds at 50° C. and 1 minute at 72° C.

5'-GATGCCGACCTCCAAGATGA-3' (SEQ ID NO: 33)

5'-CATGCCCACCGCCAGTA-3, (SEQ ID NO: 34)
Conditions for PCR reaction are 25 cycles of 30 seconds of 94° C., 30 seconds at 60° C. and 1 minute at 72° C.

5'-CCGACTTCCGCCTGATG-3' (SEQ ID NO: 35)

5'-GGTGAGCTTGCCGATGTATT-3' (SEQ ID NO: 36)
Conditions for PCR reaction are 25 cycles of 30 seconds at 94° C., 30 seconds at 60° C. and 1 minute at 72° C.

5'-CGCGCAAACCGTCCTC-3' (SEQ ID NO: 37)

5'-AGCTTGCCGATGTATTCACC-3' (SEQ ID NO: 38)
Conditions for PCR reaction are 25 cycles of 30 seconds at 94° C., 30 seconds at 60° C. and 1 minute at 72° C.

5'-TCGCCGGCATGAGTGAAGTCGTGAA-3' (SEQ ID NO: 39)

5'-CGGCGCAATCGTTAGGCTGGTGAT-3' (SEQ ID NO: 40)
Conditions for PCR reaction are 25 cycles of 30 seconds at 94° C., 30 seconds at 65° C. and 1 minute at 72° C.

(2) ORF2-Related PCR Primers

5'-GCGCTGTTGGTGGTAG-3' (SEQ ID NO: 41)

5'-CTGGGCTGCTTGATG-3' (SEQ ID NO: 42)
Conditions for PCR reaction are 25 cycles of 30 seconds at 94° C., 30 seconds at 50° C. and 1 minute at 72° C.

5'-TTACTGGCGATGCTGA-3' (SEQ ID NO: 43)

5'-CTTGGGGATGGTTTTC-3' (SEQ ID NO: 44)
Conditions for PCR reaction are 25 cycles of 30 seconds at 94° C., 30 seconds at 50° C. and 1 minute at 72° C.

5'-GTCGCCGTTTGCCATC-3' (SEQ ID NO: 45)

5'-CGCTTGGGGATGGTTT-3' (SEQ ID NO: 46)
Conditions for PCR reaction are 25 cycles of 30 seconds at 94° C., 30 seconds at 55° C. and 1 minute at 72° C.

5'-TCGTGGCCTTCGGTTTCTTT-3' (SEQ ID NO: 47)

5'-CGCTTGGGGATGGTTTTCA-3' (SEQ ID NO: 48)
Conditions for PCR reaction are 25 cycles of 30 seconds at 94° C., 30 seconds at 65° C. and 1 minute at 72° C.

5'-CATCCGGTTGTGGGTAGTGAAGTTA-3' (SEQ ID NO: 49)

5'-GTGGCAAGGTTAGTGAGGGTGAC-3' (SEQ ID NO: 50)

Conditions for PCR reaction are 25 cycles of 30 seconds at 94° C., 30 seconds at 65° C. and 1 minute at 72° C.

(3) ORF3-Related PCR Primers

5'-GCCTTGCGCTACCTG-3' (SEQ ID NO: 51)

5'-GTGTCCGCCAGCAGT-3' (SEQ ID NO: 52)

Conditions for PCR reaction are 25 cycles of 30 seconds at 94° C., 30 seconds at 50° C. and 1 minute at 72° C.

5'-TCTTCGGCCTGACTCACCTC-3' (SEQ ID NO: 53)

5'-GCACGATGACGACGACCTG-3' (SEQ ID NO: 54)

Conditions for PCR reaction are 25 cycles of 30 seconds at 94° C., 30 seconds at 60° C. and 1 minute at 72° C.

5'-CTCGCGATGCCGTGGTTCTG-3' (SEQ ID NO: 55)

5'-CCGTGTCCGCCAGCkGTGA-3' (SEQ ID NO: 56)

Conditions for PCR reaction are 25 cycles of 30 seconds at 94° C., 30 seconds at 65° C. and 1 minute at 72° C.

5'-CCTTGCGCTACCTGATTGTTGGAG-3' (SEQ ID NO: 57)

5'-CATAATTGAGCACGATGACGACGAC-3' (SEQ ID NO: 58)

Conditions for PCR reaction are 25 cycles of 30 seconds at 94° C., 30 seconds at 65° C. and 1 minute at 72° C.

(4) ORF4-Related PCR Primers

5'-TGAATGGGCGAGTGAT-3' (SEQ ID NO: 59)

5'-GGCAGCCAAATCGTG-3' (SEQ ID NO: 60)

Conditions for PCR reaction are 25 cycles of 30 seconds at 94° C., 30 seconds at 50° C. and 1 minute at 72° C.

5'-GCCAGTGCCGCTTAT-3' (SEQ ID NO: 61)

5'-TTCTTTCTGTTCGGATTCAC-3' (SEQ ID NO: 62)

Conditions for PCR reaction are 25 cycles of 30 seconds at 94° C., 30 seconds at 50° C. and 1 minute at 72° C.

5'-GTGAATCCGAACAGAAAGAA-3' (SEQ ID NO: 63)

5'-ACAGCCAGCGAATGC-3' (SEQ ID NO: 64)

Conditions for PCR reaction are 25 cycles of 30 seconds at 94° C., 30 seconds at 50° C. and 1 minute at 72° C.

5'-GATAAGGAAGGTCGCCACTA-3' (SEQ ID NO: 65)

5'-GCAGCCAAATCGTGATG-3' (SEQ ID NO: 66)

Conditions for PCR reaction are 25 cycles of 30 seconds at 94° C., 30 seconds at 55° C. and 1 minute at 72° C.

5'-AAAGGACGAAGTGCGATTGCCAGTG-3' (SEQ ID NO: 67)

5'-CGTTCATCACAGCCAGCGAATGC-3' (SEQ ID NO: 68)

Conditions for PCR reaction are 25 cycles of 30 seconds at 94° C., 30 seconds at 65° C. and 1 minute at 72° C.

(5) ORF8-Related PCR Primers

5'-GCGACGGTCTCTGTT-3' (SEQ ID NO: 69)

5'-GTTTCTTACCCGATTGC-3' (SEQ ID NO: 70)

Conditions for PCR reaction are 25 cycles of 30 seconds at 94° C., 30 seconds at 50° C. and 1 minute at 72° C.

5'-CGACGGTCTCTGTTGAA-3' (SEQ ID NO: 71)

5'-CCACTAACTTGCCTCACAAT-3' (SEQ ID NO: 72)

Conditions for PCR reaction are 25 cycles of 30 seconds at 94° C., 30 seconds at 50° C. and 1 minute at 72° C.

5'-GCTATCGCTGTCTTTTTGAA-3' (SEQ ID NO: 73)

5'-AATTTTTCGCTCCTTTGGT-3' (SEQ ID NO: 74)

Conditions for PCR reaction are 25 cycles of 30 seconds at 94° C., 30 seconds at 60° C. and 1 minute at 72° C.

5'-TGGCAGACGTCAAGTATTTGTTCAC-3' (SEQ ID NO: 75)

5'-TCAATTTTTCGCTCCTTTGGTATGA-3' (SEQ ID NO: 76)

Conditions for PCR reaction are 25 cycles of 30 seconds at 94° C., 30 seconds at 65° C. and 1 minute at 72° C.

5'-GAAATTCATCAAGTCACGCCCTAT-3' (SEQ ID NO: 77)

5'-TCTCAATTTTTCGCTCCTTTGGTAT-3' (SEQ ID NO: 78)

Conditions for PCR reaction are 25 cycles of 30 seconds at 94° C., 30 seconds at 65° C. and 1 minute at 72° C.

---

The invention claimed is:

1. An isolated probe which consists of a nucleotide sequence consisting of at least 15 contiguous nucleotides from position 4202 to 7513 of the nucleotide sequence of SEQ ID NO: 1 or the complementary sequence thereof, wherein said probe hybridizes over its entire length to SEQ ID NO: 1.

2. The probe according to claim 1, wherein the nucleotide sequence consists of at least 15 contiguous nucleotides of the nucleotide sequence of SEQ ID NO: 2 or the complementary sequence thereof.

3. The probe according to claim 1, wherein the nucleotide sequence consists of at least 20 nucleotides.

4. The probe according to claim 1, wherein the nucleotide sequence is selected from the group consisting of the nucleotide sequences of SEQ ID NO: 11, SEQ ID NO: 12, and the complementary sequences thereof.

5. The probe according to claim 1, which is labeled.

6. A method of determining if beer-spoilage lactic acid bacterium *Lactobacillus brevis* or *Pediococcus damnosus* is present in a beer sample, the method comprising: (i) contacting a nucleic acid sample from the beer sample with the isolated probe of claim 1; (ii) detecting the presence or absence of a hybridization complex formed between said nucleic acid and said isolated probe; and (iii) determining that beer-spoilage lactic acid bacterium *Lactobacillus brevis* or *Pediococcus damnosus* is present in the sample when said hybridization complex is present.

7. The method according to claim 6, wherein the nucleic acid sample is isolated from a colony of bacteria obtained from beer.

8. An isolated polynucleotide primer pair, wherein the first primer consists of at least 15 contiguous nucleotides of the nucleotide sequence from position 4202 to position 7513 of SEQ ID NO: 1, and the second primer consists of at least 15 contiguous nucleotides of the sequence complementary to the nucleotide sequence from position 4202 to position 7513 of the nucleotide sequence of SEQ ID NO: 1, and wherein said primer pair amplifies SEQ ID NO: 1 and the complementary sequence thereof.

9. The primer pair according to claim 8, wherein the first primer consists of at least 15 contiguous nucleotides of the nucleotide sequence of SEQ ID NO: 2 and the second primer consists of at least 15 contiguous nucleotides of the sequence complementary to the nucleotide sequence of SEQ ID NO: 2.

10. The primer pair according to claim 8, wherein the contiguous nucleotides are at least 20 contiguous nucleotides.

11. The primer pair according to claim 8, wherein the two primers are selected from the group consisting of the nucleotide sequences of SEQ ID NO: 11, SEQ ID NO: 12, and the complementary sequences thereof.

12. A method of determining if beer-spoilage lactic acid bacterium *Lactobacillus brevis* or *Pediococcus damnosus* is present in a beer sample, the method comprising: (i) amplifying a nucleic acid sample from the beer sample using the primer pair of claim 8; (ii) detecting the presence or absence of an amplification product; and (iii) determining that beer-spoilage lactic acid bacterium *Lactobacillus brevis* or *Pediococcus damnosus* is present in the nucleic acid sample when an amplification product is detected.

13. The method according to claim 12, wherein the nucleic acid sample is isolated from a colony of bacteria obtained from beer.

14. The probe according to claim 1, wherein the nucleotide sequence consists of at least 15 contiguous nucleotides of the nucleotide sequence of SEQ ID NO: 4 or the complementary sequence thereof.

15. The probe according to claim 1, wherein the nucleotide sequence is selected from the group consisting of the nucleotide sequences of SEQ ID NO: 13, SEQ ID NO: 14, and the complementary sequences thereof.

16. The primer pair according to claim 8, wherein the first primer consists of at least 15 contiguous nucleotides of the nucleotide sequence of SEQ ID NO: 4 and the second primer consists of at least 15 contiguous nucleotides of the sequence complementary to the nucleotide sequence of SEQ ID NO: 4.

17. The primer pair according to claim 8, wherein the two primers are selected from the group consisting of the nucleotide sequences of SEQ ID NO: 13, SEQ ID NO: 14, and the complementary sequences thereof.

18. The probe according to claim 1, wherein the nucleotide sequence consists of at least 15 contiguous nucleotides of the nucleotide sequence of SEQ ID NO: 6 or the complementary sequence thereof.

19. The probe according to claim 1, wherein the nucleotide sequence is selected from the group consisting of the nucleotide sequences of SEQ ID NO: 15, SEQ ID NO: 16, and the complementary sequences thereof.

20. The primer pair according to claim 8, wherein the first primer consists of at least 15 contiguous nucleotides of the nucleotide sequence of SEQ ID NO: 6 and the second primer consists of at least 15 contiguous nucleotides of the sequence complementary to the nucleotide sequence of SEQ ID NO: 6.

21. The primer pair according to claim 8, wherein the two primers are selected from the group consisting of the nucleotide sequences of SEQ ID NO: 15, SEQ ID NO: 16, and the complementary sequences thereof.

* * * * *

SEQUENCE LISTING

```
<160> NUMBER OF SEQ ID NOS: 79

<210> SEQ ID NO 1
<211> LENGTH: 8056
<212> TYPE: DNA
<213> ORGANISM: Lactobacillus brevis

<400> SEQUENCE: 1
ttagcttagc aaacaaagga ttcctgtaat tgcatgttgt atttgacttg tatcaggcaa      60
ttcttgttca tcaattaggt aattaaaact acccagaata agtgaagtta ataatgacat     120
ttcaaactta tcaggttttt cctccagcat acttacaaga ttgtttctta aaacccttt     180 tatctcacta ctcaaatctt tgctatccaa ttgaatagag cgcaatgcta aaatcttttc     240
acgttgtttg attaaaagat tttttatatc aggtgccaat atggatgtaa tgctcaaaaa     300
gttttgattt tgtttattta aattacttct tttcttcaat actgaatcat aagtcgacac     360
aaaatcctga atcattttcg cggccaagtg atacttatcc tgatagtgcc tataaaatgt     420
```

-continued

```
ctgacgattg atcaaggctt tattagagat atcaattacc gatacattat taaatccctg    480
ttgtcttact aattgtataa aagaattttc aattaacatt tctgttctct tatttcttaa    540
atcagtcata agttcctcct tttctccaaa catcagtata gatccatatg taacttaagt    600
atacacaaat aacattttgt atgcctaagt gacgtttcaa aaaagttgt ctatgtcttt     660 ccaaaataat gtccactatt attagtactt agcttaaaag ggaggaatat cagatgttcg    720
atgtaattcg tagtaaaaga tattggttag cattattgct tgttggagca attattggaa    780
tagtttcatt tgccttcatt ggcatacgta actctgtcaa agtaaaacaa attcctgtag    840
cacttgtcaa cgaagacaaa ggagctctca gcaataaaat tgaaagtaag ttgcgaaaga    900
aattcaatgg aaaagattca aaatcaaat gggtatctcc acaaaagat ggttttaatg      960 atcaaaagta ttatggggct ttcattatta gatcaggatt tcaaaagag ttacagcagc    1020 aaaatgaatc gctaaaggcc caaattatta gccaaaagct cactactctt caaaaaaagg   1080
agaaattacc agattctgca aaatcaaaat gcttcaagc taaatttaaa tcacaattgc    1140
ttcaagctaa atttgttaca cagaaacccg ttcaccctgc acagattaag atcagtatta   1200
atcaaggaat gaatgctcaa atatcgcaat tgctatccca agcacttcct aagattgcaa   1260
atgcgctttc atcacgaatt agcgcacagc aacaaagtgt tcttagcaaa aataagatta   1320
atttatccgc aaaatcttgg gatttggttt cgaccctat tagtgtatct actcatgagt    1380
ctaataaaat tgaaaagaac acggttaatg gcacagcacc catgcttcta gtggcattgg   1440
cgtggtttag cgctttaatt ccctctctta ttttatggcg cgaacacaca aaaagaagcg   1500
cttcaaaatt tttaaatgct acaacaataa ctagtcaact aattaccggt ttggtagcaa   1560
gtattctttc agcaacagtt gggttcttat ttgttaatgt atgctttaac ctaacaattc   1620
caaacccaat taactttatc ggattaatgt ctattagtat ctttgtcttt tatcttatta   1680
taacgtgtgt cctggattgg ttgggatttg ctttctaccc attactactc gtagtctggc   1740
tcctagcaat ttccgtgata tcttatgcac cggaaaccct tgatcctttg taccgaaagg   1800
gaatttacag ttgggttcca atgcgattta gcatgcaaac actaacaaat actttgtatt   1860
tccataatgg atcgagtacc accatgtcat cattattagt cttgttaata attggatttg   1920
tcgctgctat cttgatgtat agttcaggat acttaaaaca ctatttgttc acggttcgcc   1980
cacaccgcaa aattaaataa ttaaacaaaa catgaaaccc aattattcat atcattaaaa   2040
atagccaatc aattgattga ctatttttg atgatccatt tagcaacaat tccctcaaaa    2100
aaaaagagag tgtgaaatat tttgtgtaaa tgtatataaa aattctgaat tgtatagagg   2160
cagagaatgt tcttgaggta taccctattg gctaatcaca cataaaagct ttcttatatc   2220
attatttttt tggcaggtac tgtgtaggtg gaaatgaacg aatgctttaa tagttttgtg   2280
tcacaaaata aattttggag attttcagca ctccagtagt tcaatgattc ctggcatatt   2340
ccatcagcaa gtttatatat tgcgtctttt aacaattgga gcttactttc agaaactaca   2400
tgaactttaa agttggtatg tgcatctgaa gcaaagatga tagaggggtg gaaaataatg   2460
gaatagaaag tttgactctg atatttttcc gcaaaccaat tcgaagatgt agttatttgt   2520
tctacatcac ctttaaagat ttcatcacta gctcgtcgat ttttatcttc tatgacaatc   2580
tgtgtgcttt gatccagcca aagattatca ggaccgcctt ctttgatagc cgttctgcc    2640 tcaggctgac tagaatcaaa tcctaataat tctcctaatc tttgaatgct tgctctaaag   2700
tttgtttcgt cggcatagtt tgtataaagc aggtcatcat taatagctcg aatatgtgta   2760
gctaaatcat tgctatcttc gaagtcatac tttttatat atggtagatt gcaagaatta   2820
```

-continued

```
accgaacact gcgaactgct gaaaaacctt tcgtggtgat tgccaattga gtgttttcat    2880
tggtcttgca ttaatccaat gattaatttg atctaattct ttggcgctaa ccgtctcaat    2940
ttttcgctcc tttggtatga atcgccgaac gtatcggttt aatatctcat tactcccacg    3000
ttcttctggt gagtatgggt gtgcaaagta aactggaatg cctagttttt gctcgatttc    3060
atcatatttt acaaactctc gtcctcgatc aacagtgatt gacttagcat tctcgatccc    3120
ttgaaaaaaa tgaattaata ctggtgtcac tgcctgacta ttgcgaccac taacttgcct    3180
cacaatatgt tgccgactta atctttctgt gattgtgaca agcacttcac cacgtttctt    3240
acccgattgc atcgtatcaa cttcaaagtg accaaaatcc tgccgtgctt gaacactttt    3300
gggtcttgat tcaattgaac ggccgtgaac aaatacttga cgtctgccat cagactgacg    3360
tttttgacga ataccttcgt caggtaaatc agctaatgac agtttgagtc ggccagcatt    3420
gagccaatta taaatcgttt tgaaaggtaa ccctaaaaca tgagcagcag tttctggtga    3480
ccactttaaa atgccaatgt gctcattcaa aaagacagcg atagcggtg ttagtgtgtg    3540
atgacggcca cgtagatgac gttttttcaa tgccaatgca tgagcaatat cagctttata    3600
gggcgtgact tgatgaattt caacagagac cgtcgcaggt gatcggttaa taaaacgcgc    3660
gatggcacga atcgaataat tcaattccag caaagtttga atgacagtac gttcttgaga    3720
tgataaacta gtcatgagtc gcagttcctt tatggttgtt ttggacaatt accattaaag    3780
gcacaattca catagggaga agaccattga aatccaccat tttactagtc gaagacgagg    3840
cgggcttagc cgactcactc aaaaccgaat ttgagctcga gaacttcaat gtgttctggg    3900
ccaatgacgg cctaatcgcg ctggacatgt tccggcaaaa cgaggcccag attgatttaa    3960
tcattttgga ctggatgctg ccgcacattc aagatcaaga aacccagctg attactgtat    4020
tgattggcat tggctggatc gcgatggtgg cgatatcgcg ggtgtatctg cgcgaccact    4080
acctctctga tgtgctcgcc agtgtctgct tagctagccg ctggtggttg ctggtcacac    4140
ctgcggaagc ctttattcaa gctaaaatgc ggcagttttt accggaaggg atgttgaaat    4200
catggccaca tcaaaattaa cgattgttgt tcctgcttac aatgaagaag aggtgctgac    4260
gtcctcggtg caaaaattac tggccgttga agaccaaatc gccgcgcaaa ccgtcctcgg    4320
tcagcgtgcc gacatcctga tcgtcgatga tggttccatg gatcacacct gggacatcat    4380
cgaaaaactg cacgccatga attctcgcgt gcgcggactg cgttttttccc gcaacttcgg    4440
ccaccagtcg gcgctgatcg ccggcatgag tgaagtcgtg aaaaccgccg atatgattgt    4500
caccatcgat gccgacctcc aagatgatcc cgacaaaatc ggcgacatgg tggatgccta    4560
tgcggatggc gccgacatcg tctacggcgt ccggaacaac cgggaaaccg acagctggtt    4620
caagcgcacc acgcccaag gctactacaa gacactcaag ctgctgggcg tcgaactcgt    4680
gcccaatcac gccgacttcc gcctgatgtc caagcgcgcc gttgaaacct tcctgcagta    4740
tccagaacgc aacattttca ttcgcggcct gattcctaag ctcggcttca aaactgccga    4800
agtcttctac aagcgcacac cgcgcatggc cggcgaatcc aagtacccgc tgaaaaagat    4860
gctggctttt gcctgggacg gcatcaccag cctaacgatt gcgccggtgc ggctcattct    4920
cattctgggt accttgtctt gcctactggc ggtgggcatg gtggtttacg ccattgtcat    4980
gaaaatgctg gggctcaccg tgcacggctg gtcgttgttg atggtgtcgc tgtggttcgt    5040
tggcggcatc caaatgatca gcctcggggt gattggtgaa tacatcggca agctccaccac    5100
cgaagttaaa catcgcccgc gctacacggt gcaaacgatt ctggattgag gtgagggtat    5160
gaaaaagatt aaacccgcct ttctgccagc aattttaatc ctctgcctgc tcattggcag    5220
```

-continued

```
catcggtaac ctgaccagtg tgctcggggt gccggcgctg ttggtggtag tgctcctggg   5280
cgcggggctt tacttcgggg cgccccgact tgaccatttg tctacaaggc agctgcgctg   5340
gggcattggc cttggcttac tggcgatgct gattgcccag gtggtcgtgt tgcacgtgat   5400
gcccaacacc gtttaccacg atccgtaccg ggtactgtcg caagccgacc agctcgccgc   5460
cggccacatg acctgggata tcacctactt ctggcgctac gccaataacg tgccgctggc   5520
ttatctgctc tccctgtggt tgcggctgac gcaactggtg ggcttaagca ccaatctttc   5580
ggtgcacctg ctgagtatct tggtgttgga cagctttatt gccctggcgc tgcatacgat   5640
ttggcagctc agccagcgcg ccagcctgct ggtcgtggcc ttcggtttct ttgccttgtc   5700
gccgtttgcc tacacctact acctgcaagt cttttactcc gacttaccga cgatgctggt   5760
gctgctcatc atcatacgca gcctgctgaa ctggtcgcag aaaacatcgc gccagcgctg   5820
gtttgccggc agcggactag ttgttgccgt gatgctcggc gccatgctca agcctaatct   5880
ggtggtcttg ttgccagctc tgctgattgt cggcctgatt ctggcccgtc agcacctctg   5940
gcgacaagcc aaactgaccc tgcccatcct cttgattgtg ctgggcttcg ggctgagtct   6000
gccggcgacc aaagtctttg acgtggcagc caattatcaa ccccgcaccg ccttttcgtt   6060
cccggcgacc cactggatct tgatgggcta caaccagcac agcaacggcg gctactccgg   6120
caaggatgtc ggacgtgcca tcaagcagcc cagccaagcc gaccgccagc ggtacaattt   6180
gaaaaccatc cccaagcgca tcaaaactct cggggtggtt ggcgtcatcc ggttgtgggt   6240
agtgaagtta ggcatcgtgc tcaatgtcca aggcattcag cgctggtaca acggcggctt   6300
ccgcgccgcg cctagttggt acagtaatca tgctggcttc tatcagggac tgaccgtgat   6360
tggctatgtg gccgcgaccc tgctcatgtg gggcgcactg atgctgaagc tcttgcggtg   6420
gcggccagat ctgaccgacc cgcatcaaat ccttgcactg ctggcggtga ccactgccct   6480
tggctacctg gctttccaca ccctactgtg ggaagttgaa ccgcgctatg gtcaagccat   6540
tttgccgctg ctctgggtgg cttttggcgg catcccgcgt caggccagcc agtcgcgtcc   6600
ccgctgggcg aaccaagcta gcctcctcaa tggcgccact gcttcactcg tcgcctttgg   6660
ggccgctggt gtgcttggcg ctcagctgcc acaaaagcaa gtgattgccg cccagcgcag   6720
tcagctatcc gtgcagtatc acgccaagcc caagaccgtg acgccaggca ccgtgctggc   6780
agaggtggtc gatgtgaacg cgccagcgaa ctatttttcc gttcagattc atgctggtag   6840
tcaggtgcaa gtcaccctca ctaaccttgc caccgggcaa cattatcggt taacgatggc   6900
tggcagtgtg gcccgcctgc accaccagct cgccgctggg caatatcgga ttaccgttca   6960
aaacctcacc acccgcggcc agcaggtcga tgtgacccac acctaccatt atcagctcgc   7020
tgctcacccg ctaacggtga acggccaatc gcagcccacc gcctcgttga tttatacctg   7080
catgcagcgc tgagaaagga gccttttat ggaaaaacca atcactaccc tttacagcaa   7140
atacgataca gccttgcgct acctgattgt tggaggcctc accaccggca ttaatgtggt   7200
gctgttcttc ggcctgactc acctcgcgat gccgtggttc tgggcgaaca ttatcgcctg   7260
ggtcctcagc gtgctgtttg ccttcattgc caacaagaaa gtcgtgttca actccgccga   7320
catgaccttc cggactgtgg tcaaagaagg cgccagcttc ttcaccttgc gcggcgcgtc   7380
actgctggcg gacacggcga ttttgttcat cggcctcacc ttaatgcacg ttcgccgct   7440 gattgtgaag ctgatcgacc aggtcgtcgt catcgtgctc aattatggct tcagcaaact   7500
aattttcgct taacgtaaaa atggtcccag cagtggaaac tgccgagacc atttttgcttg   7560 gctagccaag cttgatgccg gcatccgcca gcgctgcgtc gaccacgttc atcacagcca   7620
```

-continued

```
gcgaatgcgc catccgctgc ttggcggcag ccaaatcgtg atgcgcaatc atcgtttcga    7680
acgcgacgaa ctcttcgtac atgcggtgcc ggtcagctac ataccttga tcgacaaaat     7740 tttcttgcac atattttgtc agtaattctt tctgttcgga ttcacttaat tctaccggta    7800
aagccacgtt aaactctttt gcataccgtg agtttgattt acgatctttc ttttcaactt    7860
cattccacaa ctgctctcga tcactcgccc attcaggtga attttttggc gtcaaaataa    7920
agctttctgg catgatcgat cgggcataaa aatagtggcg accttcctta tcatcaaata    7980
gcttttcacc acttcgataa gcggcactgg caatcgcact tcgtcctta ccagcactaa     8040 tattactaaa actcat                                                    8056
```

<210> SEQ ID NO 2
<211> LENGTH: 948
<212> TYPE: DNA
<213> ORGANISM: Lactobacillus brevis
<220> FEATURE:
<221> NAME/KEY: CDS
<222> LOCATION: (1)..(945)

<400> SEQUENCE: 2

```
atg gcc aca tca aaa tta acg att gtt gtt cct gct tac aat gaa gaa      48
Met Ala Thr Ser Lys Leu Thr Ile Val Val Pro Ala Tyr Asn Glu Glu
 1               5                  10                  15 gag gtg ctg acg tcc tcg gtg caa aaa tta ctg gcc gtt gaa gac caa      96
Glu Val Leu Thr Ser Ser Val Gln Lys Leu Leu Ala Val Glu Asp Gln
             20                  25                  30 atc gcc gcg caa acc gtc ctc ggt cag cgt gcc gac atc ctg atc gtc     144
Ile Ala Ala Gln Thr Val Leu Gly Gln Arg Ala Asp Ile Leu Ile Val
         35                  40                  45 gat gat ggt tcc atg gat cac acc tgg gac atc atc gaa aaa ctg cac     192
Asp Asp Gly Ser Met Asp His Thr Trp Asp Ile Ile Glu Lys Leu His
     50                  55                  60 gcc atg aat tct cgc gtg cgc gga ctg cgt ttt tcc cgc aac ttc ggc     240
Ala Met Asn Ser Arg Val Arg Gly Leu Arg Phe Ser Arg Asn Phe Gly
 65                  70                  75                  80 cac cag tcg gcg ctg atc gcc ggc atg agt gaa gtc gtg aaa acc gcc     288
His Gln Ser Ala Leu Ile Ala Gly Met Ser Glu Val Val Lys Thr Ala
                 85                  90                  95 gat atg att gtc acc atc gat gcc gac ctc caa gat gat ccc gac aaa     336
Asp Met Ile Val Thr Ile Asp Ala Asp Leu Gln Asp Asp Pro Asp Lys
            100                 105                 110 atc ggc gac atg gtg gat gcc tat gcg gat ggc gcc gac atc gtc tac     384
Ile Gly Asp Met Val Asp Ala Tyr Ala Asp Gly Ala Asp Ile Val Tyr
        115                 120                 125 ggc gtc cgg aac aac cgg gaa acc gac agc tgg ttc aag cgc acc acg     432
Gly Val Arg Asn Asn Arg Glu Thr Asp Ser Trp Phe Lys Arg Thr Thr
    130                 135                 140 gcc caa ggc tac tac aag aca ctc aag ctg ctg ggc gtc gaa ctc gtg     480
Ala Gln Gly Tyr Tyr Lys Thr Leu Lys Leu Leu Gly Val Glu Leu Val
145                 150                 155                 160 ccc aat cac gcc gac ttc cgc ctg atg tcc aag cgc gcc gtt gaa acc     528
Pro Asn His Ala Asp Phe Arg Leu Met Ser Lys Arg Ala Val Glu Thr
                165                 170                 175 ttc ctg cag tat cca gaa cgc aac att ttc att cgc ggc ctg att cct     576
Phe Leu Gln Tyr Pro Glu Arg Asn Ile Phe Ile Arg Gly Leu Ile Pro
            180                 185                 190 aag ctc ggc ttc aaa act gcc gaa gtc ttc tac aag cgc aca ccg cgc     624
Lys Leu Gly Phe Lys Thr Ala Glu Val Phe Tyr Lys Arg Thr Pro Arg
        195                 200                 205
```

```
atg gcc ggc gaa tcc aag tac ccg ctg aaa aag atg ctg gct ttt gcc      672
Met Ala Gly Glu Ser Lys Tyr Pro Leu Lys Lys Met Leu Ala Phe Ala
210                 215                 220 tgg gac ggc atc acc agc cta acg att gcg ccg gtg cgg ctc att ctc      720
Trp Asp Gly Ile Thr Ser Leu Thr Ile Ala Pro Val Arg Leu Ile Leu
225                 230                 235                 240 att ctg ggt acc ttg tct tgc cta ctg gcg gtg ggc atg gtg gtt tac      768
Ile Leu Gly Thr Leu Ser Cys Leu Leu Ala Val Gly Met Val Val Tyr
                245                 250                 255 gcc att gtc atg aaa atg ctg ggg ctc acc gtg cac ggc tgg tcg ttg      816
Ala Ile Val Met Lys Met Leu Gly Leu Thr Val His Gly Trp Ser Leu
            260                 265                 270 ttg atg gtg tcg ctg tgg ttc gtt ggc ggc atc caa atg atc agc ctc      864
Leu Met Val Ser Leu Trp Phe Val Gly Gly Ile Gln Met Ile Ser Leu
        275                 280                 285 ggg gtg att ggt gaa tac atc ggc aag ctc acc acc gaa gtt aaa cat      912
Gly Val Ile Gly Glu Tyr Ile Gly Lys Leu Thr Thr Glu Val Lys His
    290                 295                 300 cgc ccg cgc tac acg gtg caa acg att ctg gat tga                      948
Arg Pro Arg Tyr Thr Val Gln Thr Ile Leu Asp
305                 310                 315

<210> SEQ ID NO 3
<211> LENGTH: 315
<212> TYPE: PRT
<213> ORGANISM: Lactobacillus brevis

<400> SEQUENCE: 3

Met Ala Thr Ser Lys Leu Thr Ile Val Val Pro Ala Tyr Asn Glu Glu
 1               5                  10                  15

Glu Val Leu Thr Ser Ser Val Gln Lys Leu Leu Ala Val Glu Asp Gln
            20                  25                  30

Ile Ala Ala Gln Thr Val Leu Gly Gln Arg Ala Asp Ile Leu Ile Val
        35                  40                  45

Asp Asp Gly Ser Met Asp His Thr Trp Asp Ile Ile Glu Lys Leu His
    50                  55                  60

Ala Met Asn Ser Arg Val Arg Gly Leu Arg Phe Ser Arg Asn Phe Gly
65                  70                  75                  80

His Gln Ser Ala Leu Ile Ala Gly Met Ser Glu Val Val Lys Thr Ala
                85                  90                  95

Asp Met Ile Val Thr Ile Asp Ala Asp Leu Gln Asp Asp Pro Asp Lys
            100                 105                 110

Ile Gly Asp Met Val Asp Ala Tyr Ala Asp Gly Ala Asp Ile Val Tyr
        115                 120                 125

Gly Val Arg Asn Asn Arg Glu Thr Asp Ser Trp Phe Lys Arg Thr Thr
    130                 135                 140

Ala Gln Gly Tyr Tyr Lys Thr Leu Lys Leu Leu Gly Val Glu Leu Val
145                 150                 155                 160

Pro Asn His Ala Asp Phe Arg Leu Met Ser Lys Arg Ala Val Glu Thr
                165                 170                 175

Phe Leu Gln Tyr Pro Glu Arg Asn Ile Phe Ile Arg Gly Leu Ile Pro
            180                 185                 190

Lys Leu Gly Phe Lys Thr Ala Glu Val Phe Tyr Lys Arg Thr Pro Arg
        195                 200                 205

Met Ala Gly Glu Ser Lys Tyr Pro Leu Lys Lys Met Leu Ala Phe Ala
    210                 215                 220
```

Trp Asp Gly Ile Thr Ser Leu Thr Ile Ala Pro Val Arg Leu Ile Leu
225                 230                 235                 240

Ile Leu Gly Thr Leu Ser Cys Leu Leu Ala Val Gly Met Val Val Tyr
            245                 250                 255

Ala Ile Val Met Lys Met Leu Gly Leu Thr Val His Gly Trp Ser Leu
        260                 265                 270

Leu Met Val Ser Leu Trp Phe Val Gly Gly Ile Gln Met Ile Ser Leu
    275                 280                 285

Gly Val Ile Gly Glu Tyr Ile Gly Lys Leu Thr Thr Glu Val Lys His
290                 295                 300

Arg Pro Arg Tyr Thr Val Gln Thr Ile Leu Asp
305                 310                 315

<210> SEQ ID NO 4
<211> LENGTH: 1935
<212> TYPE: DNA
<213> ORGANISM: Lactobacillus brevis
<220> FEATURE:
<221> NAME/KEY: CDS
<222> LOCATION: (1)..(1932)

<400> SEQUENCE: 4 atg aaa aag att aaa ccc gcc ttt ctg cca gca att tta atc ctc tgc      48
Met Lys Lys Ile Lys Pro Ala Phe Leu Pro Ala Ile Leu Ile Leu Cys
1               5                   10                  15 ctg ctc att ggc agc atc ggt aac ctg acc agt gtg ctc ggg gtg ccg      96
Leu Leu Ile Gly Ser Ile Gly Asn Leu Thr Ser Val Leu Gly Val Pro
                20                  25                  30 gcg ctg ttg gtg gta gtg ctc ctg ggc gcg ggg ctt tac ttc ggg gcg     144
Ala Leu Leu Val Val Val Leu Leu Gly Ala Gly Leu Tyr Phe Gly Ala
            35                  40                  45 ccc cga ctt gac cat ttg tct aca agg cag ctg cgc tgg ggc att ggc     192
Pro Arg Leu Asp His Leu Ser Thr Arg Gln Leu Arg Trp Gly Ile Gly
        50                  55                  60 ctt ggc tta ctg gcg atg ctg att gcc cag gtg gtc gtg ttg cac gtg     240
Leu Gly Leu Leu Ala Met Leu Ile Ala Gln Val Val Val Leu His Val
65                  70                  75                  80 atg ccc aac acc gtt tac cac gat ccg tac cgg gta ctg tcg caa gcc     288
Met Pro Asn Thr Val Tyr His Asp Pro Tyr Arg Val Leu Ser Gln Ala
                85                  90                  95 gac cag ctc gcc gcc ggc cac atg acc tgg gat atc acc tac ttc tgg     336
Asp Gln Leu Ala Ala Gly His Met Thr Trp Asp Ile Thr Tyr Phe Trp
            100                 105                 110 cgc tac gcc aat aac gtg ccg ctg gct tat ctg ctc tcc ctg tgg ttg     384
Arg Tyr Ala Asn Asn Val Pro Leu Ala Tyr Leu Leu Ser Leu Trp Leu
        115                 120                 125 cgg ctg acg caa ctg gtg ggc tta agc acc aat ctt tcg gtg cac ctg     432
Arg Leu Thr Gln Leu Val Gly Leu Ser Thr Asn Leu Ser Val His Leu
    130                 135                 140 ctg agt atc ttg gtg ttg gac agc ttt att gcc ctg gcg ctg cat acg     480
Leu Ser Ile Leu Val Leu Asp Ser Phe Ile Ala Leu Ala Leu His Thr
145                 150                 155                 160 att tgg cag ctc agc cag cgc gcc agc ctg ctg gtc gtg gcc ttc ggt     528
Ile Trp Gln Leu Ser Gln Arg Ala Ser Leu Leu Val Val Ala Phe Gly
                165                 170                 175 ttc ttt gcc ttg tcg ccg ttt gcc tac acc tac tac ctg caa gtc ttt     576
Phe Phe Ala Leu Ser Pro Phe Ala Tyr Thr Tyr Tyr Leu Gln Val Phe
            180                 185                 190

```
tac tcc gac tta ccg acg atg ctg gtg ctg ctc atc atc ata cgc agc      624
Tyr Ser Asp Leu Pro Thr Met Leu Val Leu Leu Ile Ile Ile Arg Ser
            195                 200                 205 ctg ctg aac tgg tcg cag aaa aca tcg cgc cag cgc tgg ttt gcc ggc      672
Leu Leu Asn Trp Ser Gln Lys Thr Ser Arg Gln Arg Trp Phe Ala Gly
    210                 215                 220 agc gga cta gtt gtt gcc gtg atg ctc ggc gcc atg ctc aag cct aat      720
Ser Gly Leu Val Val Ala Val Met Leu Gly Ala Met Leu Lys Pro Asn
225                 230                 235                 240 ctg gtg gtc ttg ttg cca gct ctg ctg att gtc ggc ctg att ctg gcc      768
Leu Val Val Leu Leu Pro Ala Leu Leu Ile Val Gly Leu Ile Leu Ala
                245                 250                 255 cgt cag cac ctc tgg cga caa gcc aaa ctg acc ctg ccc atc ctc ttg      816
Arg Gln His Leu Trp Arg Gln Ala Lys Leu Thr Leu Pro Ile Leu Leu
        260                 265                 270 att gtg ctg ggc ttc ggg ctg agt ctg ccg gcg acc aaa gtc ttt gac      864
Ile Val Leu Gly Phe Gly Leu Ser Leu Pro Ala Thr Lys Val Phe Asp
    275                 280                 285 gtg gca gcc aat tat caa ccc cgc acc gcc ttt tcg ttc ccg gcg acc      912
Val Ala Ala Asn Tyr Gln Pro Arg Thr Ala Phe Ser Phe Pro Ala Thr
290                 295                 300 cac tgg atc ttg atg ggc tac aac cag cac agc aac ggc ggc tac tcc      960
His Trp Ile Leu Met Gly Tyr Asn Gln His Ser Asn Gly Gly Tyr Ser
305                 310                 315                 320 ggc aag gat gtc gga cgt gcc atc aag cag ccc agc caa gcc gac cgc     1008
Gly Lys Asp Val Gly Arg Ala Ile Lys Gln Pro Ser Gln Ala Asp Arg
                325                 330                 335 cag cgg tac aat ttg aaa acc atc ccc aag cgc atc aaa act ctc ggg     1056
Gln Arg Tyr Asn Leu Lys Thr Ile Pro Lys Arg Ile Lys Thr Leu Gly
        340                 345                 350 gtg gtt ggc gtc atc cgg ttg tgg gta gtg aag tta ggc atc gtg ctc     1104
Val Val Gly Val Ile Arg Leu Trp Val Val Lys Leu Gly Ile Val Leu
    355                 360                 365 aat gtc caa ggc att cag cgc tgg tac aac ggc ggc ttc cgc gcc gcg     1152
Asn Val Gln Gly Ile Gln Arg Trp Tyr Asn Gly Gly Phe Arg Ala Ala
370                 375                 380 cct agt tgg tac agt aat cat gct ggc ttc tat cag gga ctg acc gtg     1200
Pro Ser Trp Tyr Ser Asn His Ala Gly Phe Tyr Gln Gly Leu Thr Val
385                 390                 395                 400 att ggc tat gtg gcc gcg acc ctg ctc atg tgg ggc gca ctg atg ctg     1248
Ile Gly Tyr Val Ala Ala Thr Leu Leu Met Trp Gly Ala Leu Met Leu
                405                 410                 415 aag ctc ttg cgg tgg cgg cca gat ctg acc gac ccg cat caa atc ctt     1296
Lys Leu Leu Arg Trp Arg Pro Asp Leu Thr Asp Pro His Gln Ile Leu
        420                 425                 430 gca ctg ctg gcg gtg acc act gcc ctt ggc tac ctg gct ttc cac acc     1344
Ala Leu Leu Ala Val Thr Thr Ala Leu Gly Tyr Leu Ala Phe His Thr
    435                 440                 445 cta ctg tgg gaa gtt gaa ccg cgc tat ggt caa gcc att ttg ccg ctg     1392
Leu Leu Trp Glu Val Glu Pro Arg Tyr Gly Gln Ala Ile Leu Pro Leu
450                 455                 460 ctc tgg gtg gct ttg gcg gcc atc ccg cgt cag gcc agc cag tcg cgt     1440
Leu Trp Val Ala Leu Ala Ala Ile Pro Arg Gln Ala Ser Gln Ser Arg
465                 470                 475                 480 ccc cgc tgg gcg aac caa gct agc ctc ctc aat ggc gcc act gct tca     1488
Pro Arg Trp Ala Asn Gln Ala Ser Leu Leu Asn Gly Ala Thr Ala Ser
                485                 490                 495 ctc gtc gcc ttt ggg gcc gct ggt gtg ctt ggc gct cag ctg cca caa     1536
Leu Val Ala Phe Gly Ala Ala Gly Val Leu Gly Ala Gln Leu Pro Gln
        500                 505                 510
```

-continued

| | | |
|---|---|---|
| aag caa gtg att gcc gcc cag cgc agt cag cta tcc gtg cag tat cac<br>Lys Gln Val Ile Ala Ala Gln Arg Ser Gln Leu Ser Val Gln Tyr His<br>     515                    520                    525 | 1584 |
| gcc aag ccc aag acc gtg acg cca ggc acc gtg ctg gca gag gtg gtc<br>Ala Lys Pro Lys Thr Val Thr Pro Gly Thr Val Leu Ala Glu Val Val<br>530                        535                    540 | 1632 |
| gat gtg aac gcg cca gcg aac tat ttt tcc gtt cag att cat gct ggt<br>Asp Val Asn Ala Pro Ala Asn Tyr Phe Ser Val Gln Ile His Ala Gly<br>545                       550                    555                  560 | 1680 |
| agt cag gtg caa gtc acc ctc act aac ctt gcc acc ggg caa cat tat<br>Ser Gln Val Gln Val Thr Leu Thr Asn Leu Ala Thr Gly Gln His Tyr<br>                 565                    570                    575 | 1728 |
| cgg tta acg atg gct ggc agt gtg gcc cgc ctg cac cac cag ctc gcc<br>Arg Leu Thr Met Ala Gly Ser Val Ala Arg Leu His His Gln Leu Ala<br>580                       585                    590 | 1776 |
| gct ggg caa tat cgg att acc gtt caa aac ctc acc acc cgc ggc cag<br>Ala Gly Gln Tyr Arg Ile Thr Val Gln Asn Leu Thr Thr Arg Gly Gln<br>     595                    600                    605 | 1824 |
| cag gtc gat gtg acc cac acc tac cat tat cag ctc gct gct cac ccg<br>Gln Val Asp Val Thr His Thr Tyr His Tyr Gln Leu Ala Ala His Pro<br>610                       615                    620 | 1872 |
| cta acg gtg aac ggc caa tcg cag ccc acc gcc tcg ttg att tat acc<br>Leu Thr Val Asn Gly Gln Ser Gln Pro Thr Ala Ser Leu Ile Tyr Thr<br>625                       630                    635                  640 | 1920 |
| tgc atg cag cgc tga<br>Cys Met Gln Arg | 1935 |

<210> SEQ ID NO 5
<211> LENGTH: 644
<212> TYPE: PRT
<213> ORGANISM: Lactobacillus brevis

<400> SEQUENCE: 5

Met Lys Lys Ile Lys Pro Ala Phe Leu Pro Ala Ile Leu Ile Leu Cys
1                 5                       10                       15

Leu Leu Ile Gly Ser Ile Gly Asn Leu Thr Ser Val Leu Gly Val Pro
                 20                       25                       30

Ala Leu Leu Val Val Leu Leu Gly Ala Gly Leu Tyr Phe Gly Ala
                 35                       40                       45

Pro Arg Leu Asp His Leu Ser Thr Arg Gln Leu Arg Trp Gly Ile Gly
          50                       55                       60

Leu Gly Leu Leu Ala Met Leu Ile Ala Gln Val Val Leu His Val
65                 70                       75                       80

Met Pro Asn Thr Val Tyr His Asp Pro Tyr Arg Val Leu Ser Gln Ala
                 85                       90                       95

Asp Gln Leu Ala Ala Gly His Met Thr Trp Asp Ile Thr Tyr Phe Trp
                100                     105                    110

Arg Tyr Ala Asn Asn Val Pro Leu Ala Tyr Leu Leu Ser Leu Trp Leu
          115                    120                    125

Arg Leu Thr Gln Leu Val Gly Leu Ser Thr Asn Leu Ser Val His Leu
    130                    135                    140

Leu Ser Ile Leu Val Leu Asp Ser Phe Ile Ala Leu Ala Leu His Thr
145               150                    155                  160

Ile Trp Gln Leu Ser Gln Arg Ala Ser Leu Leu Val Val Ala Phe Gly
                165                     170                    175

Phe Phe Ala Leu Ser Pro Phe Ala Tyr Thr Tyr Tyr Leu Gln Val Phe
          180                    185                    190

-continued

```
Tyr Ser Asp Leu Pro Thr Met Leu Val Leu Ile Ile Ile Arg Ser
    195                 200                 205

Leu Leu Asn Trp Ser Gln Lys Thr Ser Arg Gln Arg Trp Phe Ala Gly
210                 215                 220

Ser Gly Leu Val Val Ala Val Met Leu Gly Ala Met Leu Lys Pro Asn
225                 230                 235                 240

Leu Val Val Leu Leu Pro Ala Leu Leu Ile Val Gly Leu Ile Leu Ala
                245                 250                 255

Arg Gln His Leu Trp Arg Gln Ala Lys Leu Thr Leu Pro Ile Leu Leu
                260                 265                 270

Ile Val Leu Gly Phe Gly Leu Ser Leu Pro Ala Thr Lys Val Phe Asp
                275                 280                 285

Val Ala Ala Asn Tyr Gln Pro Arg Thr Ala Phe Ser Phe Pro Ala Thr
290                 295                 300

His Trp Ile Leu Met Gly Tyr Asn Gln His Ser Asn Gly Gly Tyr Ser
305                 310                 315                 320

Gly Lys Asp Val Gly Arg Ala Ile Lys Gln Pro Ser Gln Ala Asp Arg
                325                 330                 335

Gln Arg Tyr Asn Leu Lys Thr Ile Pro Lys Arg Ile Lys Thr Leu Gly
                340                 345                 350

Val Val Gly Val Ile Arg Leu Trp Val Val Lys Leu Gly Ile Val Leu
                355                 360                 365

Asn Val Gln Gly Ile Gln Arg Trp Tyr Asn Gly Gly Phe Arg Ala Ala
                370                 375                 380

Pro Ser Trp Tyr Ser Asn His Ala Gly Phe Tyr Gln Gly Leu Thr Val
385                 390                 395                 400

Ile Gly Tyr Val Ala Ala Thr Leu Leu Met Trp Gly Ala Leu Met Leu
                405                 410                 415

Lys Leu Leu Arg Trp Arg Pro Asp Leu Thr Asp Pro His Gln Ile Leu
                420                 425                 430

Ala Leu Leu Ala Val Thr Thr Ala Leu Gly Tyr Leu Ala Phe His Thr
                435                 440                 445

Leu Leu Trp Glu Val Glu Pro Arg Tyr Gly Gln Ala Ile Leu Pro Leu
                450                 455                 460

Leu Trp Val Ala Leu Ala Ala Ile Pro Arg Gln Ala Ser Gln Ser Arg
465                 470                 475                 480

Pro Arg Trp Ala Asn Gln Ala Ser Leu Leu Asn Gly Ala Thr Ala Ser
                485                 490                 495

Leu Val Ala Phe Gly Ala Ala Gly Val Leu Gly Ala Gln Leu Pro Gln
                500                 505                 510

Lys Gln Val Ile Ala Ala Gln Arg Ser Gln Leu Ser Val Gln Tyr His
                515                 520                 525

Ala Lys Pro Lys Thr Val Thr Pro Gly Thr Val Leu Ala Glu Val Val
                530                 535                 540

Asp Val Asn Ala Pro Ala Asn Tyr Phe Ser Val Gln Ile His Ala Gly
545                 550                 555                 560

Ser Gln Val Gln Val Thr Leu Thr Asn Leu Ala Thr Gly Gln His Tyr
                565                 570                 575

Arg Leu Thr Met Ala Gly Ser Val Ala Arg Leu His His Gln Leu Ala
                580                 585                 590

Ala Gly Gln Tyr Arg Ile Thr Val Gln Asn Leu Thr Thr Arg Gly Gln
                595                 600                 605
```

```
Gln Val Asp Val Thr His Thr Tyr His Tyr Gln Leu Ala Ala His Pro
    610                 615                 620

Leu Thr Val Asn Gly Gln Ser Gln Pro Thr Ala Ser Leu Ile Tyr Thr
625                 630                 635                 640

Cys Met Gln Arg

<210> SEQ ID NO 6
<211> LENGTH: 405
<212> TYPE: DNA
<213> ORGANISM: Lactobacillus brevis
<220> FEATURE:
<221> NAME/KEY: CDS
<222> LOCATION: (1)..(402)

<400> SEQUENCE: 6 atg gaa aaa cca atc act acc ctt tac agc aaa tac gat aca gcc ttg      48
Met Glu Lys Pro Ile Thr Thr Leu Tyr Ser Lys Tyr Asp Thr Ala Leu
  1               5                  10                  15 cgc tac ctg att gtt gga ggc ctc acc acc ggc att aat gtg gtg ctg      96
Arg Tyr Leu Ile Val Gly Gly Leu Thr Thr Gly Ile Asn Val Val Leu
             20                  25                  30 ttc ttc ggc ctg act cac ctc gcg atg ccg tgg ttc tgg gcg aac att     144
Phe Phe Gly Leu Thr His Leu Ala Met Pro Trp Phe Trp Ala Asn Ile
         35                  40                  45 atc gcc tgg gtc ctc agc gtg ctg ttt gcc ttc att gcc aac aag aaa     192
Ile Ala Trp Val Leu Ser Val Leu Phe Ala Phe Ile Ala Asn Lys Lys
     50                  55                  60 gtc gtg ttc aac tcc gcc gac atg acc ttc cgg act gtg gtc aaa gaa     240
Val Val Phe Asn Ser Ala Asp Met Thr Phe Arg Thr Val Val Lys Glu
 65                  70                  75                  80 ggc gcc agc ttc ttc acc ttg cgc ggc gcg tca ctg ctg gcg gac acg     288
Gly Ala Ser Phe Phe Thr Leu Arg Gly Ala Ser Leu Leu Ala Asp Thr
                 85                  90                  95 gcg att ttg ttc atc ggc ctc acc tta atg cac ggt tcg ccg ctg att     336
Ala Ile Leu Phe Ile Gly Leu Thr Leu Met His Gly Ser Pro Leu Ile
            100                 105                 110 gtg aag ctg atc gac cag gtc gtc gtc atc gtg ctc aat tat ggc ttc     384
Val Lys Leu Ile Asp Gln Val Val Val Ile Val Leu Asn Tyr Gly Phe
        115                 120                 125 agc aaa cta att ttc gct taa                                         405
Ser Lys Leu Ile Phe Ala
    130

<210> SEQ ID NO 7
<211> LENGTH: 134
<212> TYPE: PRT
<213> ORGANISM: Lactobacillus brevis

<400> SEQUENCE: 7

Met Glu Lys Pro Ile Thr Thr Leu Tyr Ser Lys Tyr Asp Thr Ala Leu
  1               5                  10                  15

Arg Tyr Leu Ile Val Gly Gly Leu Thr Thr Gly Ile Asn Val Val Leu
             20                  25                  30

Phe Phe Gly Leu Thr His Leu Ala Met Pro Trp Phe Trp Ala Asn Ile
         35                  40                  45

Ile Ala Trp Val Leu Ser Val Leu Phe Ala Phe Ile Ala Asn Lys Lys
     50                  55                  60

Val Val Phe Asn Ser Ala Asp Met Thr Phe Arg Thr Val Val Lys Glu
 65                  70                  75                  80
```

```
Gly Ala Ser Phe Phe Thr Leu Arg Gly Ala Ser Leu Leu Ala Asp Thr
                85                  90                  95

Ala Ile Leu Phe Ile Gly Leu Thr Leu Met His Gly Ser Pro Leu Ile
            100                 105                 110

Val Lys Leu Ile Asp Gln Val Val Val Ile Val Leu Asn Tyr Gly Phe
        115                 120                 125

Ser Lys Leu Ile Phe Ala
    130

<210> SEQ ID NO 8
<211> LENGTH: 10
<212> TYPE: DNA
<213> ORGANISM: Lactobacillus brevis

<400> SEQUENCE: 8
actgcgacca                                                          10

<210> SEQ ID NO 9
<211> LENGTH: 10
<212> TYPE: DNA
<213> ORGANISM: Lactobacillus brevis

<400> SEQUENCE: 9
ggatcgtcgg                                                          10

<210> SEQ ID NO 10
<211> LENGTH: 10
<212> TYPE: DNA
<213> ORGANISM: Lactobacillus brevis

<400> SEQUENCE: 10
agtgcacacc                                                          10

<210> SEQ ID NO 11
<211> LENGTH: 20
<212> TYPE: DNA
<213> ORGANISM: Lactobacillus brevis

<400> SEQUENCE: 11
gtcagcgtgc cgacatcctg                                               20

<210> SEQ ID NO 12
<211> LENGTH: 20
<212> TYPE: DNA
<213> ORGANISM: Lactobacillus brevis

<400> SEQUENCE: 12
tgtattcacc aatcaccccg                                               20

<210> SEQ ID NO 13
<211> LENGTH: 20
<212> TYPE: DNA
<213> ORGANISM: Lactobacillus brevis

<400> SEQUENCE: 13
gccccgactt gaccatttgt                                               20

<210> SEQ ID NO 14
<211> LENGTH: 20
<212> TYPE: DNA
<213> ORGANISM: Lactobacillus brevis
```

<400> SEQUENCE: 14
ttagcgggtg agcagcgagc                                               20

<210> SEQ ID NO 15
<211> LENGTH: 20
<212> TYPE: DNA
<213> ORGANISM: Lactobacillus brevis

<400> SEQUENCE: 15
acagccttgc gctacctgat                                               20

<210> SEQ ID NO 16
<211> LENGTH: 20
<212> TYPE: DNA
<213> ORGANISM: Lactobacillus brevis

<400> SEQUENCE: 16
ttcacaatca gcggcgaacc                                               20

<210> SEQ ID NO 17
<211> LENGTH: 20
<212> TYPE: DNA
<213> ORGANISM: Lactobacillus brevis

<400> SEQUENCE: 17
tgagttttag taatattagt                                               20

<210> SEQ ID NO 18
<211> LENGTH: 20
<212> TYPE: DNA
<213> ORGANISM: Lactobacillus brevis

<400> SEQUENCE: 18
agccaagctt gatgccggca                                               20

<210> SEQ ID NO 19
<211> LENGTH: 20
<212> TYPE: DNA
<213> ORGANISM: Lactobacillus brevis

<400> SEQUENCE: 19
aaagtaactt agaaaaacaa                                               20

<210> SEQ ID NO 20
<211> LENGTH: 20
<212> TYPE: DNA
<213> ORGANISM: Lactobacillus brevis

<400> SEQUENCE: 20
atgatctacg gactttacct                                               20

<210> SEQ ID NO 21
<211> LENGTH: 25
<212> TYPE: DNA
<213> ORGANISM: Lactobacillus brevis

<400> SEQUENCE: 21
tcaatatgaa aaactagtcg agcag                                         25

<210> SEQ ID NO 22
<211> LENGTH: 24
<212> TYPE: DNA
<213> ORGANISM: Lactobacillus brevis

```
<400> SEQUENCE: 22
ttatggacgt taacatagtc agca                                              24

<210> SEQ ID NO 23
<211> LENGTH: 25
<212> TYPE: DNA
<213> ORGANISM: Lactobacillus brevis

<400> SEQUENCE: 23
ggaagatgct cagtgggacc gaatc                                             25

<210> SEQ ID NO 24
<211> LENGTH: 23
<212> TYPE: DNA
<213> ORGANISM: Lactobacillus brevis

<400> SEQUENCE: 24 gcctttgat gcgctcgaac gat                                                23

<210> SEQ ID NO 25
<211> LENGTH: 25
<212> TYPE: DNA
<213> ORGANISM: Lactobacillus brevis

<400> SEQUENCE: 25
tcacagaaag attaagtcgg caaca                                             25

<210> SEQ ID NO 26
<211> LENGTH: 24
<212> TYPE: DNA
<213> ORGANISM: Lactobacillus brevis

<400> SEQUENCE: 26
tctaattctt tggcgctaac cgtc                                              24

<210> SEQ ID NO 27
<211> LENGTH: 25
<212> TYPE: DNA
<213> ORGANISM: Lactobacillus brevis

<400> SEQUENCE: 27
aattgaaagt aagttgcgaa agaaa                                             25

<210> SEQ ID NO 28
<211> LENGTH: 20
<212> TYPE: DNA
<213> ORGANISM: Lactobacillus brevis

<400> SEQUENCE: 28
ggcgaaccgt gaacaaatag                                                   20

<210> SEQ ID NO 29
<211> LENGTH: 25
<212> TYPE: DNA
<213> ORGANISM: Lactobacillus brevis

<400> SEQUENCE: 29
tacaattagt aagacaacag ggatt                                             25

<210> SEQ ID NO 30
<211> LENGTH: 20
<212> TYPE: DNA
<213> ORGANISM: Lactobacillus brevis
```

<210> SEQ ID NO 31
<211> LENGTH: 16
<212> TYPE: DNA
<213> ORGANISM: Lactobacillus brevis

<400> SEQUENCE: 31
ttactggccg ttgaag                                                     16

<210> SEQ ID NO 32
<211> LENGTH: 15
<212> TYPE: DNA
<213> ORGANISM: Lactobacillus brevis

<400> SEQUENCE: 32
tgagcttgcc gatgt                                                      15

<210> SEQ ID NO 33
<211> LENGTH: 20
<212> TYPE: DNA
<213> ORGANISM: Lactobacillus brevis

<400> SEQUENCE: 33
gatgccgacc tccaagatga                                                 20

<210> SEQ ID NO 34
<211> LENGTH: 18
<212> TYPE: DNA
<213> ORGANISM: Lactobacillus brevis

<400> SEQUENCE: 34
catgcccacc gccagtag                                                   18

<210> SEQ ID NO 35
<211> LENGTH: 17
<212> TYPE: DNA
<213> ORGANISM: Lactobacillus brevis

<400> SEQUENCE: 35
ccgacttccg cctgatg                                                    17

<210> SEQ ID NO 36
<211> LENGTH: 20
<212> TYPE: DNA
<213> ORGANISM: Lactobacillus brevis

<400> SEQUENCE: 36
ggtgagcttg ccgatgtatt                                                 20

<210> SEQ ID NO 37
<211> LENGTH: 16
<212> TYPE: DNA
<213> ORGANISM: Lactobacillus brevis

<400> SEQUENCE: 37
cgcgcaaacc gtcctc                                                     16

<210> SEQ ID NO 38
<211> LENGTH: 20
<212> TYPE: DNA
<213> ORGANISM: Lactobacillus brevis

<400> SEQUENCE: 30
tcaggcaatt cttgttcatc                                                 20

```
<400> SEQUENCE: 38
agcttgccga tgtattcacc                                              20

<210> SEQ ID NO 39
<211> LENGTH: 25
<212> TYPE: DNA
<213> ORGANISM: Lactobacillus brevis

<400> SEQUENCE: 39
tcgccggcat gagtgaagtc gtgaa                                        25

<210> SEQ ID NO 40
<211> LENGTH: 24
<212> TYPE: DNA
<213> ORGANISM: Lactobacillus brevis

<400> SEQUENCE: 40
cggcgcaatc gttaggctgg tgat                                         24

<210> SEQ ID NO 41
<211> LENGTH: 16
<212> TYPE: DNA
<213> ORGANISM: Lactobacillus brevis

<400> SEQUENCE: 41
gcgctgttgg tggtag                                                  16

<210> SEQ ID NO 42
<211> LENGTH: 15
<212> TYPE: DNA
<213> ORGANISM: Lactobacillus brevis

<400> SEQUENCE: 42
ctgggctgct tgatg                                                   15

<210> SEQ ID NO 43
<211> LENGTH: 16
<212> TYPE: DNA
<213> ORGANISM: Lactobacillus brevis

<400> SEQUENCE: 43
ttactggcga tgctga                                                  16

<210> SEQ ID NO 44
<211> LENGTH: 16
<212> TYPE: DNA
<213> ORGANISM: Lactobacillus brevis

<400> SEQUENCE: 44
cttggggatg gttttc                                                  16

<210> SEQ ID NO 45
<211> LENGTH: 16
<212> TYPE: DNA
<213> ORGANISM: Lactobacillus brevis

<400> SEQUENCE: 45
gtcgccgttt gccatc                                                  16

<210> SEQ ID NO 46
<211> LENGTH: 16
<212> TYPE: DNA
<213> ORGANISM: Lactobacillus brevis
```

<400> SEQUENCE: 46
cgcttgggga tggttt                                                    16

<210> SEQ ID NO 47
<211> LENGTH: 20
<212> TYPE: DNA
<213> ORGANISM: Lactobacillus brevis

<400> SEQUENCE: 47
tcgtggcctt cggtttcttt                                                20

<210> SEQ ID NO 48
<211> LENGTH: 19
<212> TYPE: DNA
<213> ORGANISM: Lactobacillus brevis

<400> SEQUENCE: 48
cgcttgggga tggttttca                                                 19

<210> SEQ ID NO 49
<211> LENGTH: 25
<212> TYPE: DNA
<213> ORGANISM: Lactobacillus brevis

<400> SEQUENCE: 49
catccggttg tgggtagtga agtta                                          25

<210> SEQ ID NO 50
<211> LENGTH: 23
<212> TYPE: DNA
<213> ORGANISM: Lactobacillus brevis

<400> SEQUENCE: 50
gtggcaaggt tagtgagggt gac                                            23

<210> SEQ ID NO 51
<211> LENGTH: 15
<212> TYPE: DNA
<213> ORGANISM: Lactobacillus brevis

<400> SEQUENCE: 51
gccttgcgct acctg                                                     15

<210> SEQ ID NO 52
<211> LENGTH: 15
<212> TYPE: DNA
<213> ORGANISM: Lactobacillus brevis

<400> SEQUENCE: 52
gtgtccgcca gcagt                                                     15

<210> SEQ ID NO 53
<211> LENGTH: 20
<212> TYPE: DNA
<213> ORGANISM: Lactobacillus brevis

<400> SEQUENCE: 53
tcttcggcct gactcacctc                                                20

<210> SEQ ID NO 54
<211> LENGTH: 19
<212> TYPE: DNA
<213> ORGANISM: Lactobacillus brevis

<400> SEQUENCE: 54
gcacgatgac gacgacctg                                           19

<210> SEQ ID NO 55
<211> LENGTH: 20
<212> TYPE: DNA
<213> ORGANISM: Lactobacillus brevis

<400> SEQUENCE: 55
ctcgcgatgc cgtggttctg                                          20

<210> SEQ ID NO 56
<211> LENGTH: 19
<212> TYPE: DNA
<213> ORGANISM: Lactobacillus brevis

<400> SEQUENCE: 56
ccgtgtccgc cagcagtga                                           19

<210> SEQ ID NO 57
<211> LENGTH: 24
<212> TYPE: DNA
<213> ORGANISM: Lactobacillus brevis

<400> SEQUENCE: 57
ccttgcgcta cctgattgtt ggag                                     24

<210> SEQ ID NO 58
<211> LENGTH: 25
<212> TYPE: DNA
<213> ORGANISM: Lactobacillus brevis

<400> SEQUENCE: 58
cataattgag cacgatgacg acgac                                    25

<210> SEQ ID NO 59
<211> LENGTH: 16
<212> TYPE: DNA
<213> ORGANISM: Lactobacillus brevis

<400> SEQUENCE: 59
tgaatgggcg agtgat                                              16

<210> SEQ ID NO 60
<211> LENGTH: 15
<212> TYPE: DNA
<213> ORGANISM: Lactobacillus brevis

<400> SEQUENCE: 60
ggcagccaaa tcgtg                                               15

<210> SEQ ID NO 61
<211> LENGTH: 15
<212> TYPE: DNA
<213> ORGANISM: Lactobacillus brevis

<400> SEQUENCE: 61
gccagtgccg cttat                                               15

<210> SEQ ID NO 62
<211> LENGTH: 20
<212> TYPE: DNA
<213> ORGANISM: Lactobacillus brevis -continued

```
<400> SEQUENCE: 62
ttctttctgt tcggattcac                                              20

<210> SEQ ID NO 63
<211> LENGTH: 20
<212> TYPE: DNA
<213> ORGANISM: Lactobacillus brevis

<400> SEQUENCE: 63
gtgaatccga acagaaagaa                                              20

<210> SEQ ID NO 64
<211> LENGTH: 15
<212> TYPE: DNA
<213> ORGANISM: Lactobacillus brevis

<400> SEQUENCE: 64
acagccagcg aatgc                                                   15

<210> SEQ ID NO 65
<211> LENGTH: 20
<212> TYPE: DNA
<213> ORGANISM: Lactobacillus brevis

<400> SEQUENCE: 65
gataaggaag gtcgccacta                                              20

<210> SEQ ID NO 66
<211> LENGTH: 17
<212> TYPE: DNA
<213> ORGANISM: Lactobacillus brevis

<400> SEQUENCE: 66
gcagccaaat cgtgatg                                                 17

<210> SEQ ID NO 67
<211> LENGTH: 25
<212> TYPE: DNA
<213> ORGANISM: Lactobacillus brevis

<400> SEQUENCE: 67
aaaggacgaa gtgcgattgc cagtg                                        25

<210> SEQ ID NO 68
<211> LENGTH: 23
<212> TYPE: DNA
<213> ORGANISM: Lactobacillus brevis

<400> SEQUENCE: 68
cgttcatcac agccagcgaa tgc                                          23

<210> SEQ ID NO 69
<211> LENGTH: 15
<212> TYPE: DNA
<213> ORGANISM: Lactobacillus brevis

<400> SEQUENCE: 69
gcgacggtct ctgtt                                                   15

<210> SEQ ID NO 70
<211> LENGTH: 17
<212> TYPE: DNA
<213> ORGANISM: Lactobacillus brevis
```

```
<400> SEQUENCE: 70
gtttcttacc cgattgc                                                  17

<210> SEQ ID NO 71
<211> LENGTH: 17
<212> TYPE: DNA
<213> ORGANISM: Lactobacillus brevis

<400> SEQUENCE: 71
cgacggtctc tgttgaa                                                  17

<210> SEQ ID NO 72
<211> LENGTH: 20
<212> TYPE: DNA
<213> ORGANISM: Lactobacillus brevis

<400> SEQUENCE: 72
ccactaactt gcctcacaat                                               20

<210> SEQ ID NO 73
<211> LENGTH: 20
<212> TYPE: DNA
<213> ORGANISM: Lactobacillus brevis

<400> SEQUENCE: 73
gctatcgctg tcttttgaa                                                20

<210> SEQ ID NO 74
<211> LENGTH: 19
<212> TYPE: DNA
<213> ORGANISM: Lactobacillus brevis

<400> SEQUENCE: 74
aatttttcgc tcctttggt                                                19

<210> SEQ ID NO 75
<211> LENGTH: 25
<212> TYPE: DNA
<213> ORGANISM: Lactobacillus brevis

<400> SEQUENCE: 75
tggcagacgt caagtatttg ttcac                                         25

<210> SEQ ID NO 76
<211> LENGTH: 25
<212> TYPE: DNA
<213> ORGANISM: Lactobacillus brevis

<400> SEQUENCE: 76 tcaattttc gctcctttgg tatga                                          25

<210> SEQ ID NO 77
<211> LENGTH: 24
<212> TYPE: DNA
<213> ORGANISM: Lactobacillus brevis

<400> SEQUENCE: 77
gaaattcatc aagtcacgcc ctat                                          24

<210> SEQ ID NO 78
<211> LENGTH: 25
<212> TYPE: DNA
<213> ORGANISM: Lactobacillus brevis
```

```
<400> SEQUENCE: 78 tctcaattttt tcgctccttt ggtat                                          25

<210> SEQ ID NO 79
<211> LENGTH: 9901
<212> TYPE: DNA
<213> ORGANISM: Lactobacillus brevis

<400> SEQUENCE: 79
atcacttgct ggttgctttc tagatgaatt ttcggaacgc taaacattgg aatccctctc      60
ttcgattgat ggttgcggta acttcaatct aacagattgg gtttcttttt ttatcaccca     120
acaggtgaaa agtgaaaaca ttagacaacg ttgatactac agtaactgtc gtaaattttg     180
ggatttatat gaataattcc aggtttagct tagcaaacaa aggattcctg taattgcatg     240
ttgtatttga cttgtatcag gcaattcttg ttcatcaatt aggtaattaa aactacccag     300
aataagtgaa gttaataatg acatttcaaa cttatcaggt ttttcctcca gcatacttac     360
aagattgttt cttaaaaccc ttttatctc actactcaaa tctttgctat ccaattgaat      420
agagcgcaat gctaaaatct tttcacgttg tttgattaaa agatttttta tatcaggtgc     480
caatatggat gtaatgctca aaaagttttg attttgttta tttaaattac ttcttttctt     540
caatactgaa tcataagtcg acacaaaatc ctgaatcatt ttcgcggcca agtgatactt     600
atcctgatag tgcctataaa atgtctgacg attgatcaag gctttattag agatatcaat     660
taccgataca ttattaaatc cctgttgtct tactaattgt ataaaagaat tttcaattaa     720
catttctgtt ctcttatttc ttaaatcagt cataagttcc tccttttctc caaacatcag     780
tatagatcca tatgtaactt aagtatacac aaataacatt ttgtatgcct aagtgacgtt     840
tcaaaaaaag ttgtctatgt cttccaaaaa taatgtccac tattattagt acttagctta     900
aaagggagga atatcagatg ttcgatgtaa ttcgtagtaa aagatattgg ttagcattat     960
tgcttgttgg agcaattatt ggaatagttt catttgcctt cattggcata cgtaactctg    1020
tcaaagtaaa acaaattcct gtagcacttg tcaacgaaga caaggagct ctcagcaata     1080 aaattgaaag taagttgcga agaaaattca atggaaaaga ttcaaaaatc aaatgggtat    1140
ctccacaaaa agatggtttt aatgatcaaa agtattatgg ggctttcatt attagatcag    1200 gatttttcaaa agagttacag cagcaaaatg aatcgctaaa ggcccaaatt attagccaaa   1260
agctcactac tcttcaaaaa aaggagaaat taccagattc tgcaaaatca aaattgcttc    1320
aagctaaatt taaatcacaa ttgcttcaag ctaaatttgt tacacagaaa cccgttcacc    1380
ctgcacagat taagatcagt attaatcaag gaatgaatgc tcaaatatcg caattgctat    1440
cccaagcact tcctaagatt gcaaatgcgc tttcatcacg aattagcgca cagcaacaaa    1500
gtgttcttag caaaaataag attaatttat ccgcaaaatc ttgggatttg gtttcgaccc    1560
ctattagtgt atctactcat gagtctaata aaattgaaaa gaacacggtt aatggcacag    1620
cacccatgct tctagtggca ttggcgtggt ttagcgcttt aattccctct cttattttat    1680
ggcgcgaaca cacaaaaaga agcgcttcaa aatttttaaa tgctacaaca ataactagtc    1740
aactaattac cggtttggta gcaagtattc tttcagcaac agttgggttc ttatttgtta    1800
atgtatgctt taacctaaca attccaaacc caattaactt tatcggatta atgtctatta    1860
gtatctttgt cttttatctt attataacgt gtgtcctgga ttggttggga tttgctttct    1920
acccattact actcgtagtc tggctcctag caatttccgt gatatcttat gcaccggaaa    1980
cccttgatcc tttgtaccga aagggaattt acagttgggt tccaatgcga tttagcatgc    2040
```

```
aaacactaac aaatactttg tatttccata atggatcgag taccaccatg tcatcattat    2100
tagtcttgtt aataattgga tttgtcgctg ctatcttgat gtatagttca ggatacttaa    2160
aacactattt gttcacggtt cgcccacacc gcaaaattaa ataattaaac aaaacatgaa    2220
acccaattat tcatatcatt aaaaatagcc aatcaattga ttgactattt tttgatgatc    2280
catttagcaa caattccctc aaaaaaaaag agagtgtgaa atattttgtg taaatgtata    2340
taaaaattct gaattgtata gaggcagaga atgttcttga ggtatacccct attggctaat    2400 cacacataaa agctttctta tatcattatt tttttggcag gtactgtgta ggtggaaatg    2460
aacgaatgct ttaatagttt tgtgtcacaa aataaatttt ggagattttc agcactccag    2520
tagttcaatg attcctggca tattccatca gcaagtttat atattgcgtc ttttaacaat    2580
tggagcttac tttcagaaac tacatgaact ttaaagttgg tatgtgcatc tgaagcaaag    2640
atgatagagg ggtggaaaat aatggaatag aaagtttgac tctgatattt ttccgcaaac    2700
caattcgaag atgtagttat ttgttctaca tcacctttaa agatttcatc actagctcgt    2760
cgatttttat cttctatgac aatctgtgtg ctttgatcca gccaaagatt atcaggaccg    2820
ccttctttga tagccgtttc tgcctcaggc tgactagaat caaatcctaa taattctcct    2880
aatctttgaa tgcttgctct aaagtttgtt tcgtcggcat agtttgtata aagcaggtca    2940
tcattaatag ctcgaatatg tgtagctaaa tcattgctat cttcgaagtc atactttttt    3000
atatatggta gattgcaaga attaaccgaa cactgcgaac tgctgaaaaa cctttcgtgg    3060
tgattgccaa ttgagtgttt tcattggtct tgcattaatc caatgattaa tttgatctaa    3120
ttctttggcg ctaaccgtct caattttcg ctcctttggt atgaatcgcc gaacgtatcg    3180
gtttaatatc tcattactcc cacgttcttc tggtgagtat gggtgtgcaa agtaaactgg    3240
aatgcctagt ttttgctcga tttcatcata ttttacaaac tctcgtcctc gatcaacagt    3300
gattgactta gcattctcga tcccttgaaa aaaatgaatt aatactggtg tcactgcctg    3360
actattgcga ccactaactt gcctcacaat atgttgccga cttaatcttt ctgtgattgt    3420
gacaagcact tcaccacgtt tcttacccga ttgcatcgta tcaacttcaa agtgaccaaa    3480
atcctgccgt gcttgaacac ttttgggtct tgattcaatt gaacggccgt gaacaaatac    3540
ttgacgtctg ccatcagact gacgttttg acgaatacct ttgtcaggta aatcagctaa    3600
tgacagtttg agtcggccag cattgagcca attataaatc gttttgaaag gtaaccctaa    3660
aacatgagca gcagtttctg gtgaccactt taaaatgcca atgtgctcat tcaaaaagac    3720
agcgatagct ggtgttagtg tgtgatgacg gccacgtaga tgacgttttt tcaatgccaa    3780
tgcatgagca atatcagctt tagggcgt gacttgatga atttcaacag agaccgtcgc    3840
aggtgatcgg ttaataaaac gcgcgatggc acgaatcgaa taattcaatt ccagcaaagt    3900
ttgaatgaca gtacgttctt gagatgataa actagtcatg agtcgcagtt cctttatggt    3960
tgttttggac aattaccatt aaaggcacaa ttcacatagg gagaagacca ttgaaatcca    4020 ccatttact agtcgaagac gaggcgggct tagccgactc actcaaaacc gaatttgagc    4080
tcgagaactt caatgtgttc tgggccaatg acggcctaat cgcgctggac atgttccggc    4140
aaaacgaggc ccagattgat ttaatcattt tggactggat gctgccgcac attcaagatc    4200
aagaaaccca gctgattact gtattgattg gcattggctg gatcgcgatg gtggcgatat    4260
cgcgggtgta tctgcgcgac cactacctct ctgatgtgct cgccagtgtc tgcttagcta    4320
gccgctggtg gttgctggtc acacctgcgg aagccttttat tcaagctaaa atgcggcagt    4380
ttttaccgga agggatgttg aaatcatggc cacatcaaaa ttaacgattg ttgttcctgc    4440
```

```
ttacaatgaa gaagaggtgc tgacgtcctc ggtgcaaaaa ttactggccg ttgaagacca    4500
aatcgccgcg caaaccgtcc tcggtcagcg tgccgacatc ctgatcgtcg atgatggttc    4560
catggatcac acctgggaca tcatcgaaaa actgcacgcc atgaattctc gcgtgcgcgg    4620
actgcgtttt tcccgcaact tcggccacca gtcggcgctg atcgccggca tgagtgaagt    4680
cgtgaaaacc gccgatatga ttgtcaccat cgatgccgac ctccaagatg atcccgacaa    4740
aatcggcgac atggtggatg cctatgcgga tggcgccgac atcgtctacg gcgtccggaa    4800
caaccgggaa accgacagct ggttcaagcg caccacggcc caaggctact acaagacact    4860
caagctgctg ggcgtcgaac tcgtgcccaa tcacgccgac ttccgcctga tgtccaagcg    4920
cgccgttgaa accttcctgc agtatccaga acgcaacatt ttcattcgcg gcctgattcc    4980
taagctcggc ttcaaaactg ccgaagtctt ctacaagcgc acaccgcgca tggccggcga    5040
atccaagtac ccgctgaaaa agatgctggc ttttgcctgg gacggcatca ccagcctaac    5100
gattgcgccg gtgcggctca ttctcattct gggtaccttg tcttgcctac tggcggtggg    5160
catggtggtt tacgccattg tcatgaaaat gctgggctc accgtgcacg gctggtcgtt    5220
gttgatggtg tcgctgtggt tcgttggcgg catccaaatg atcagcctcg ggtgattgg    5280 tgaatacatc ggcaagctca ccaccgaagt taaacatcgc ccgcgctaca cggtgcaaac    5340
gattctggat tgaggtgagg gtatgaaaaa gattaaaccc gcctttctgc cagcaatttt    5400
aatcctctgc ctgctcattg gcagcatcgg taacctgacc agtgtgctcg gggtgccggc    5460
gctgttggtg gtagtgctcc tgggcgcggg gctttacttc ggggcgcccc gacttgacca    5520
tttgtctaca aggcagctgc gctggggcat tggccttggc ttactggcga tgctgattgc    5580
ccaggtggtc gtgttgcacg tgatgcccaa caccgtttac cacgatccgt accgggtact    5640
gtcgcaagcc gaccagctcg ccgccggcca catgacctgg gatatcacct acttctggcg    5700
ctacgccaat aacgtgccgc tggcttatct gctctccctg tggttgcggc tgacgcaact    5760
ggtgggctta agcaccaatc tttcggtgca cctgctgagt atcttggtgt tggacagctt    5820
tattgccctg cgctgcata cgatttggca gctcagccag cgcgccagcc tgctggtcgt    5880
ggccttcggt ttctttgcct tgtcgccgtt tgcctacacc tactacctgc aagtcttttta    5940 ctccgactta ccgacgatgc tggtgctgct catcatcata cgcagcctgc tgaactggtc    6000
gcagaaaaca tcgcgccagc gctggttttgc cggcagcgga ctagttgttg ccgtgatgct    6060
cggcgccatg ctcaagccta atctggtggt cttgttgcca gctctgctga ttgtcggcct    6120
gattctggcc cgtcagcacc tctggcgaca agccaaactg accctgccca tcctcttgat    6180
tgtgctgggc ttcgggctga gtctgccggc gaccaaagtc tttgacgtgg cagccaatta    6240
tcaaccccgc accgcctttt cgttcccggc gacccactgg atcttgatgg gctacaacca    6300
gcacagcaac ggcggctact ccggcaagga tgtcggacgt gccatcaagc agcccagcca    6360
agccgaccgc cagcggtaca atttgaaaac catccccaag cgcatcaaaa ctctcggggt    6420
ggttggcgtc atccggttgt gggtagtgaa gttaggcatc gtgctcaatg tccaaggcat    6480
tcagcgctgg tacaacggcg gcttccgcgc gcgcgcctag tggtacagta atcatgctgg    6540
cttctatcag ggactgaccg tgattggcta tgtgccgcg accctgctca tgtggggcgc    6600
actgatgctg aagctcttgc ggtggcggcc agatctgacc gacccgcatc aaatccttgc    6660
actgctggcg gtgaccactg cccttggcta cctggctttc cacaccctac tgtgggaagt    6720
tgaaccgcgc tatggtcaag ccatttttgcc gctgctctgg gtggctttgg cggccatccc    6780
gcgtcaggcc agccagtcgc gtccccgctg ggcgaaccaa gctagcctcc tcaatggcgc    6840
```

```
cactgcttca ctcgtcgcct ttggggccgc tggtgtgctt ggcgctcagc tgccacaaaa   6900
gcaagtgatt gccgcccagc gcagtcagct atccgtgcag tatcacgcca agcccaagac   6960
cgtgacgcca ggcaccgtgc tggcagaggt ggtcgatgtg aacgcgccag cgaactattt   7020
ttccgttcag attcatgctg gtagtcaggt gcaagtcacc ctcactaacc ttgccaccgg   7080
gcaacattat cggttaacga tggctggcag tgtggcccgc ctgcaccacc agctcgccgc   7140
tgggcaatat cggattaccg ttcaaaacct caccacccgc ggccagcagg tcgatgtgac   7200
ccacacctac cattatcagc tcgctgctca cccgctaacg gtgaacggcc aatcgcagcc   7260
caccgcctcg ttgatttata cctgcatgca gcgctgagaa aggagccttt ttatggaaaa   7320
accaatcact accctttaca gcaaatacga tacagccttg cgctacctga ttgttggagg   7380
cctcaccacc ggcattaatg tggtgctgtt cttcggcctg actcacctcg cgatgccgtg   7440
gttctgggcg aacattatcg cctgggtcct cagcgtgctg tttgccttca ttgccaacaa   7500
gaaagtcgtg ttcaactccg ccgacatgac cttccggact gtggtcaaag aaggcgccag   7560
cttcttcacc ttgcgcggcg cgtcactgct ggcggacacg gcgattttgt tcatcggcct   7620
caccttaatg cacggttcgc cgctgattgt gaagctgatc gaccaggtcg tcgtcatcgt   7680
gctcaattat ggcttcagca aactaatttt cgcttaacgt aaaaatggtc ccagcagtgg   7740
aaactgccga gaccattttg cttggctagc aagcttgat gccggcatcc gccagcgctg    7800
cgtcgaccac gttcatcaca gccagcgaat gcgccatccg ctgcttggcg gcagccaaat   7860
cgtgatgcgc aatcatcgtt tcgaacgcga cgaactcttc gtacatgcgg tgccggtcag   7920
ctaccatacc ttgatcgaca aaattttctt gcacatattt tgtcagtaat tctttctgtt   7980
cggattcact taattctacc ggtaaagcca cgttaaactc ttttgcatac cgtgagtttg   8040
atttacgatc tttcttttca acttcattcc acaactgctc tcgatcactc gcccattcag   8100
gtgaattttt tggcgtcaaa ataaagcttt ctggcatgat cgatcgggca taaaaatagt   8160
ggcgaccttc cttatcatca aatagctttt caccacttcg ataagcggca ctggcaatcg   8220
cacttcgtcc tttaccagca ctaatattac taaaactcat gtggaatatt gccatgtcag   8280
tcaccgtctt cctttgattc tatgggtttt gaccttgttg tcgccatcgg cgacttctaa   8340
tacaggattt tagcacgatt taccccacaa gaatttagtg gggtataagt gcgcattgac   8400
ctcgtttcac tcggccttct gattctctta actttaactt agtgtatgcc ttccgcttcg   8460
ctatttcaaa ttttatactt tgacttaacg tttcttatat gatatagttt cggtgattat   8520
ttctaatatg atttgaggga tcgttatgtc tcaaagtaac ttagaaaaac aagaagctaa   8580
attaaaagcc cttaatcaaa aaattaagga cgaaaaaaat aatattgaac aacggatagg   8640
taaacaaatc atcagtcaag ccaatttaga ttatgctaat ttgtctaacg atcagattaa   8700
gattttagcc aagcaatttt ctgaattttt aaaggtaaag tccgtagatc attagccata   8760
cgagatgggg aaattccatg tctaatcaat atgaaaaact agtcgagcag caagcgcgtt   8820
taaaacaaaa aattgagcgg gaagattta aattacggca atctaaatac tatgaaaatc    8880
ggcaagcccg caaagcccgt tctcgccgat taattcaaaa aggggcttta ttagaaaagt   8940
actttcaagc taataaccct ccggtcgaac aaaccgaaga acttttaaaa acatttgctg   9000
actatgttaa cgtccataaa ccggataaat taaaaaacga tcaacctaat aactaggccg   9060
atcgttttta ttttcaggat tgtttttttgg cttaatttct ggattgtgtt tagcaaagtc   9120
ttttaactgt tttgaattc tttgtgtaag ctctgcttta ctttctttgt gcttcctttt    9180
acttgatcgc tgttgaatta tcttttgacc cttacctctt cttttttgatt ttaggtcaag   9240
```

-continued

```
cgtaaaatct gaaattttat tttgatctag cttacttaaa tgaccgattt ctttaaagtt    9300
taaaccggct ttgggaaagc gataaatatt accaagatcg acccaggaag gtttcttcaa    9360
cccagctgat tgccaatctt gaatcggata atattgttgc ttgatataag gagacttctt    9420
ttcatactga ctagggactg tctgaaaact aaaaattcag gtataatctg aggaaaaacg    9480
aatcgaggca ttccgatgac aacacctaaa cgatacgaac tggaagatgc tcagtgggac    9540
cgaatcaaag gatacttccc gccataccgg actggccgtc catcaagcct agacaaccgt    9600
accgccctca acgctatcct ctggctcatg cgcagcgggg ctccttggcg tgatctacct    9660
gaacgctatg gctcttggaa aacggtgtat agtcgcttcc gagcctgggt aagttcaggc    9720
ttgttcgaac aggtttttct cgaattgatt gacgatctcg acatggaaaa cttgagctta    9780
gattcaacga tcgttcgagc gcatcaaaag gccactgggg caaaaaaaac gccgaatgta    9840
tggtcgaaaa tcaagctatt ggactaagtc gaggtggccg aacgaccaag attcacgcac    9900
t                                                                    9901
```